US009594975B2

(12) United States Patent
Nakashima et al.

(10) Patent No.: US 9,594,975 B2
(45) Date of Patent: Mar. 14, 2017

(54) IMAGE PROCESSING DEVICE AND SPINAL CANAL EVALUATION METHOD

(71) Applicant: HITACHI, LTD., Tokyo (JP)

(72) Inventors: Kuniyoshi Nakashima, Tokyo (JP); Tsuneto Katayama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 8 days.

(21) Appl. No.: 14/430,716

(22) PCT Filed: Oct. 23, 2013

(86) PCT No.: PCT/JP2013/078688
§ 371 (c)(1),
(2) Date: Mar. 24, 2015

(87) PCT Pub. No.: WO2014/065317
PCT Pub. Date: May 1, 2014

(65) Prior Publication Data
US 2015/0248593 A1 Sep. 3, 2015

(30) Foreign Application Priority Data

Oct. 23, 2012 (JP) ................................. 2012-233822

(51) Int. Cl.
*G06K 9/00* (2006.01)
*G06K 9/46* (2006.01)
(Continued)

(52) U.S. Cl.
CPC ............ *G06K 9/4604* (2013.01); *A61B 6/505* (2013.01); *A61B 6/5217* (2013.01);
(Continued)

(58) Field of Classification Search
None
See application file for complete search history.

(56) References Cited

U.S. PATENT DOCUMENTS 9,218,657 B2 * 12/2015 Winternheimer ..... G06T 7/0012
2009/0100105 A1 * 4/2009 Mutchler ............... G09B 23/28
(Continued)

FOREIGN PATENT DOCUMENTS

JP H4-146731 5/1992
JP 2010-29482 2/2010
(Continued)

OTHER PUBLICATIONS

J Abbas et al. "Degenerative lumbar spinal stenosis and lumbar spine configuration", Eur Spine J (2010) 19: pp. 1865-1873.*
(Continued)

*Primary Examiner* — Vu Le
*Assistant Examiner* — Samah Beg
(74) *Attorney, Agent, or Firm* — Cooper & Dunham LLP

(57) ABSTRACT

To provide an image processing device and a spinal canal evaluation method that can evaluate the spinal canal stenosis in an identified cross-sectional position, the image processing device 100 extracts a vertebral region from a series of tomographic images in which at least a part of the spine was scanned and calculates a length in the anteroposterior direction of an object for each cross section in each vertebral region. Also, a cross section including a spinous process is identified based on the calculated length in the anteroposterior direction of an object in each vertebral region, the spinal canal stenosis is evaluated by setting the identified cross-sectional position to be analyzed, and then the evaluation results are displayed. Hence, stenosis evaluation can be performed for various shapes of the spinal canal region in which a closed space hardly appears on an image due to many gaps.

11 Claims, 21 Drawing Sheets

(51) Int. Cl.
*G06T 7/00* (2006.01)
*A61B 6/00* (2006.01)
(52) U.S. Cl.
CPC ............ *G06T 7/0012* (2013.01); *A61B 6/463* (2013.01); *G06T 2207/10016* (2013.01); *G06T 2207/10072* (2013.01); *G06T 2207/20148* (2013.01); *G06T 2207/30012* (2013.01); *G06T 2207/30101* (2013.01)

(56) References Cited

U.S. PATENT DOCUMENTS

| | | | |
|---|---|---|---|
| 2011/0130653 A1* | 6/2011 | Wang | A61B 6/505 600/425 |
| 2012/0172700 A1* | 7/2012 | Krishnan | A61B 6/032 600/407 |
| 2015/0254839 A1* | 9/2015 | Yoo | G06K 9/46 382/128 |
| 2016/0045231 A1* | 2/2016 | Spitler | A61B 17/7068 606/249 |

FOREIGN PATENT DOCUMENTS

| | | |
|---|---|---|
| JP | 2011-131040 | 7/2011 |
| WO | WO 2012/118109 A1 | 9/2012 |

OTHER PUBLICATIONS

G. Karangelis and S. Zimeras. "An Accurate 3D Segmentation Method of the Spinal Canal applied to CT Data", Bildverarbeitung für die Medizin 2002, pp. 370-373.*

Y. Izci, "Chapter 30: Pediatric Spinal Tumors: Total Removal Using Laminotomy", edited by: M.A. Hayat, "Tumors of the Central Nervous System", vol. 10, Springer 2013 (originally published Dec. 22, 2012), p. 289-294.*

C. Bampis et al. "Segmentation and Extraction of the Spinal Canal in Sagittal MR Images", IEEE, SSIAI 2016, pp. 5-8.*

International Search Report in PCT/JP2013/078688.

* cited by examiner

FIG.4
<IN CASE OF EXTRACTING VERTEBRAL REGION FOR EACH SLICE>
(a)
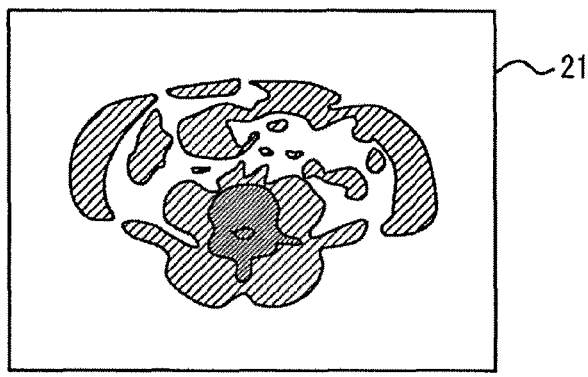
(b)
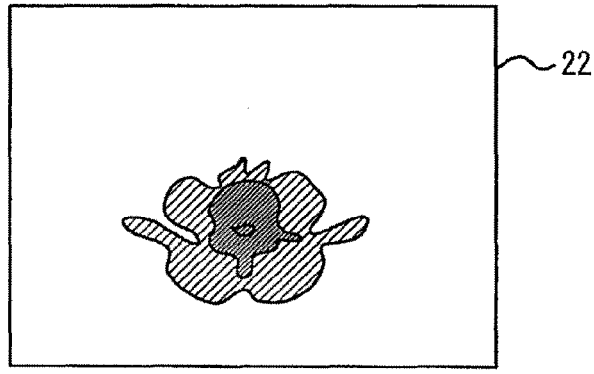
(c)
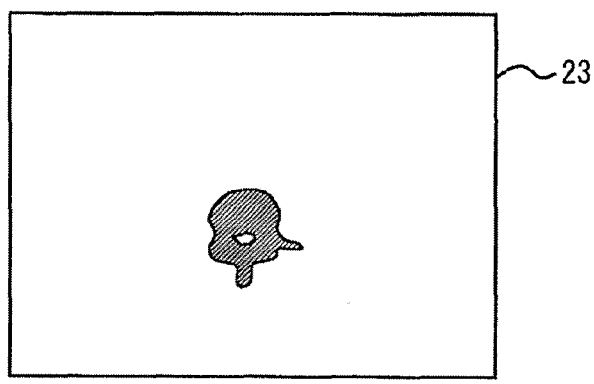

FIG.5
(a)
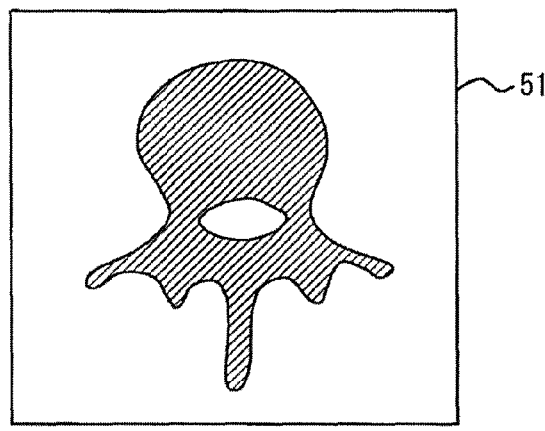
(b)
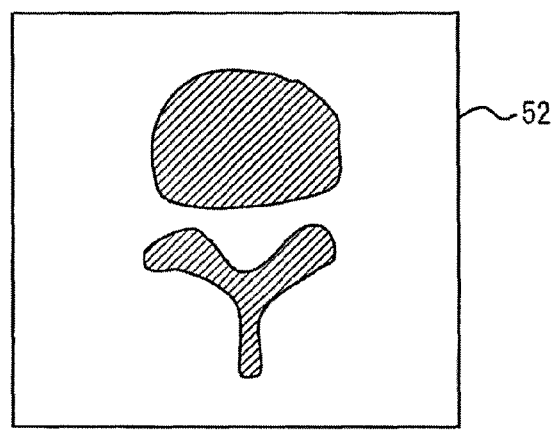
(c)
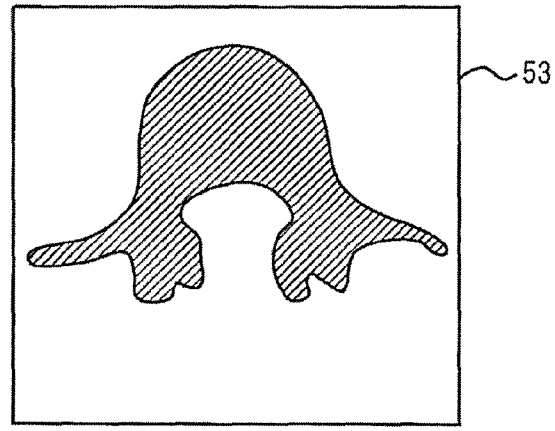

FIG.6
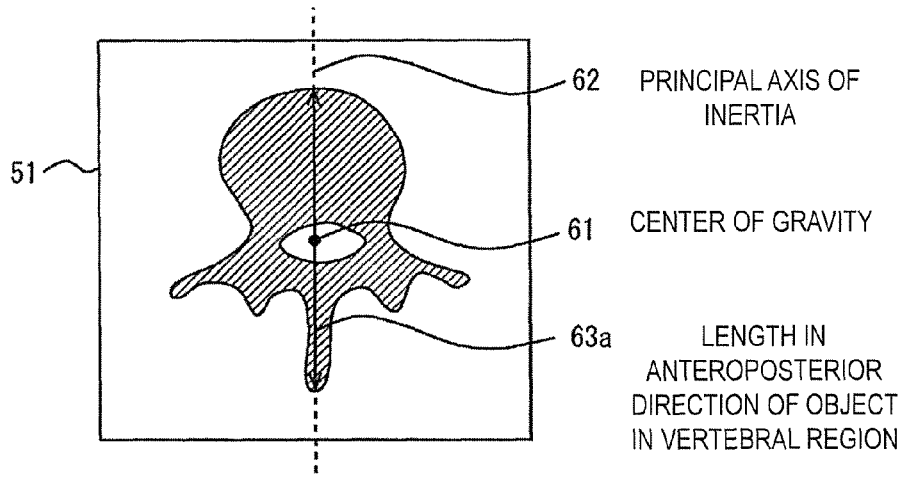
(a)
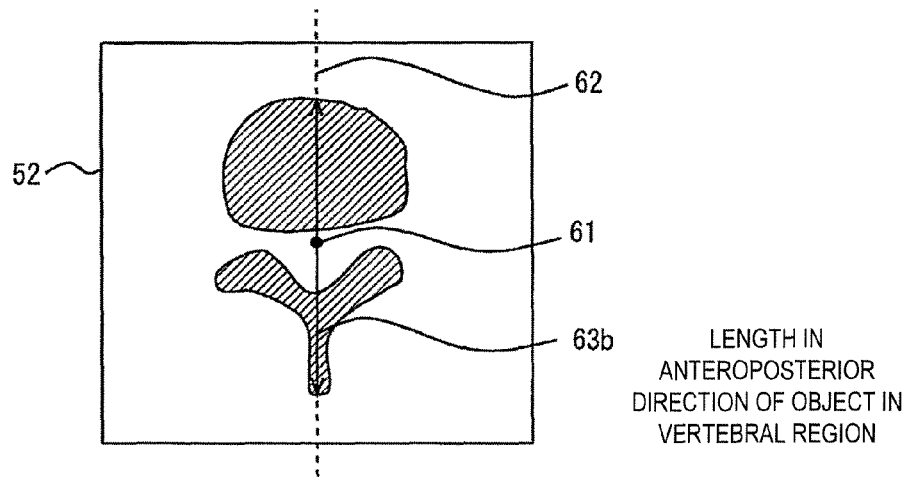
(b)
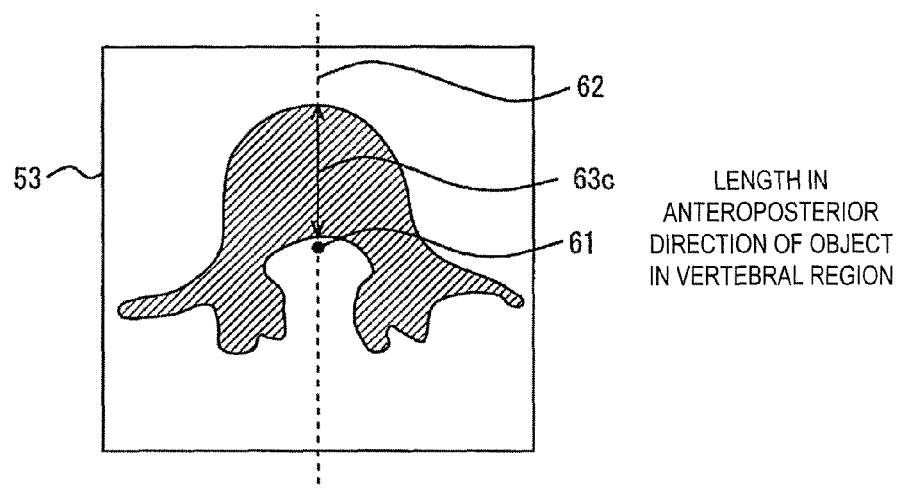
(c)

FIG.7
(a)
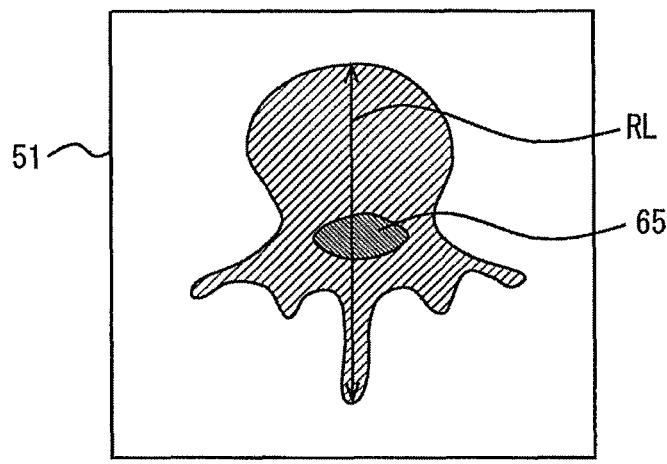
(b)
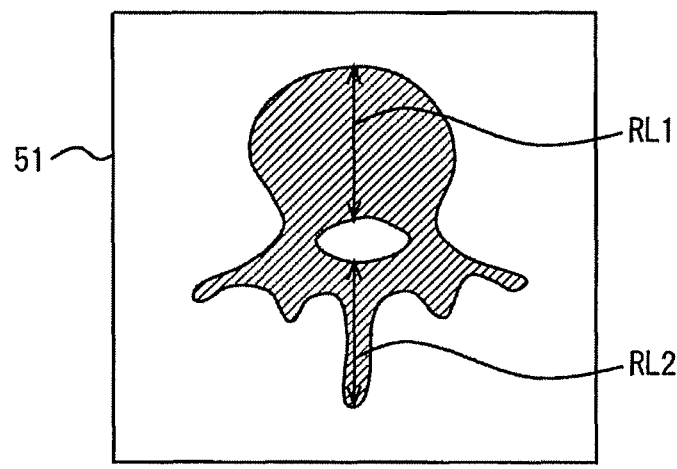

FIG.10
(a)
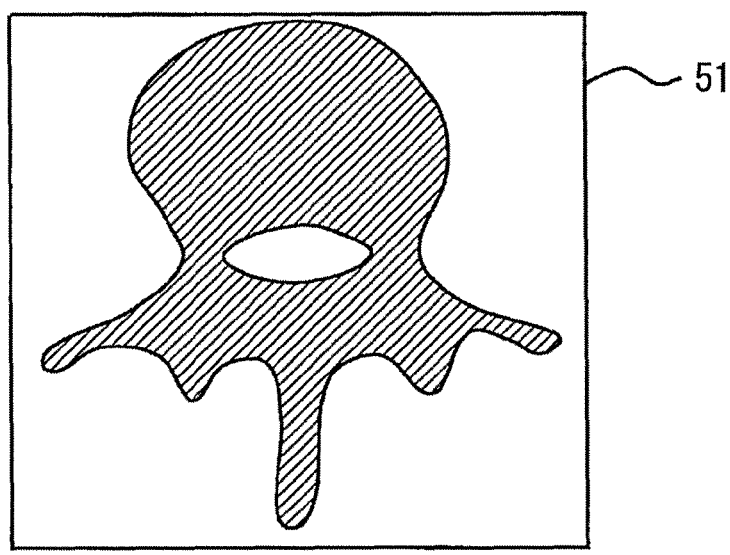
(b)
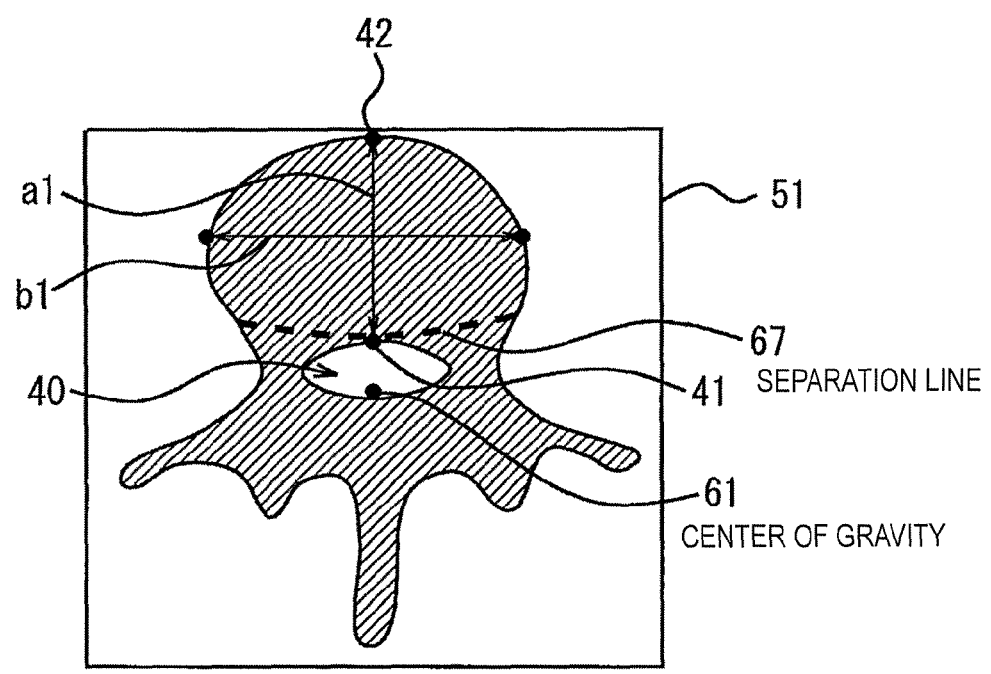

FIG.19
(a)
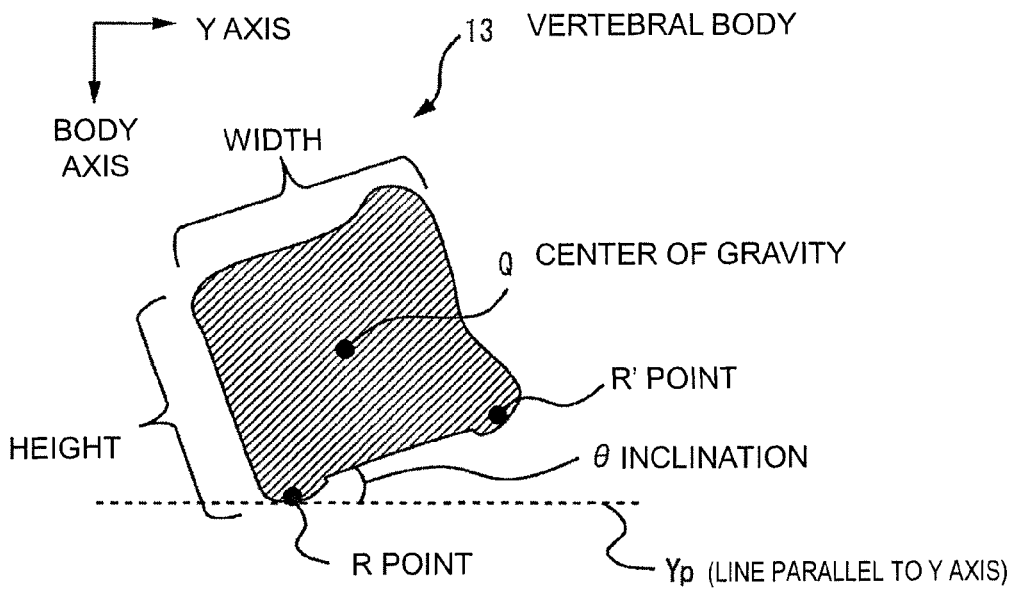
(b)
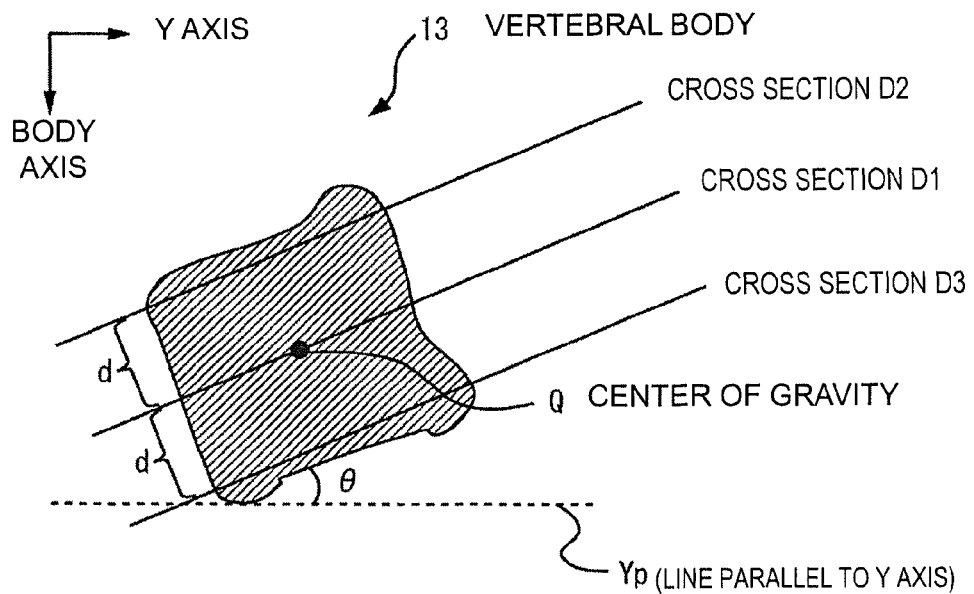

FIG.20
(a)
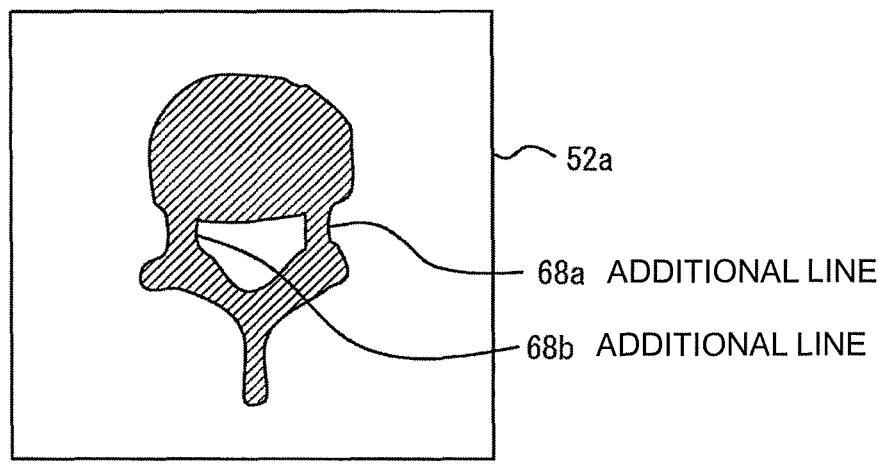
(b)
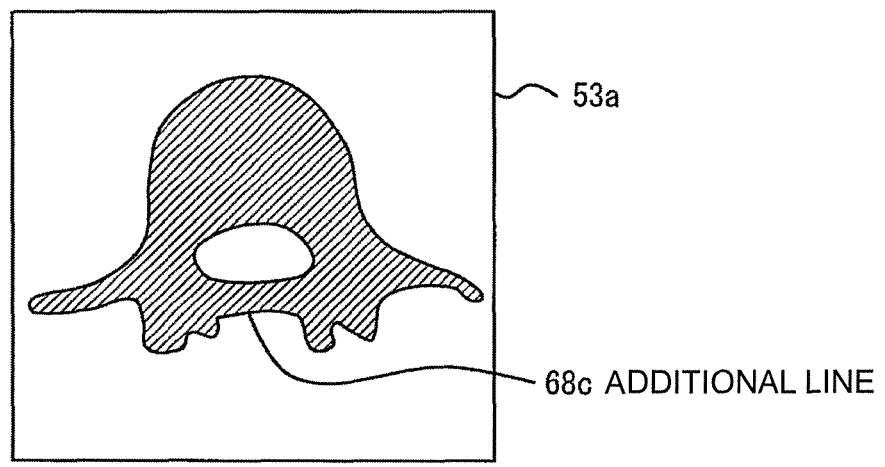

FIG.21
(a)
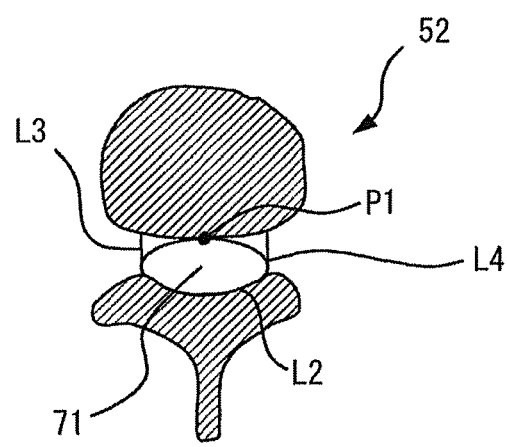
(b)
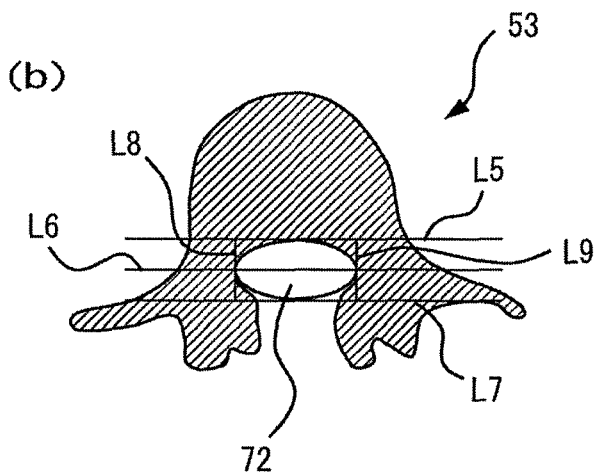

IMAGE PROCESSING DEVICE AND SPINAL CANAL EVALUATION METHOD

TECHNICAL FIELD

The present invention relates to an image processing device and a spinal canal evaluation method and, in detail, to identifying a position to be analyzed in a process of evaluating the spinal canal stenosis.

BACKGROUND ART

Conventionally, computer aided diagnosis (CAD) systems detecting and outputting a site of abnormalities from medical images scanned by an X-ray CT (Computed Tomography) apparatus, an MRI (Magnetic Resonance Imaging) apparatus, ultrasound image diagnostic apparatus, etc. have been developed. For example, in case of targeting a blood vessel, a method for calculating an index such as a stenosis rate by automatically detecting the blood vessel stenosis has been proposed (for example, see Patent Literature 1). PTL 1 describes a blood vessel stenosis rate analysis system calculating a local stenosis rate by collecting information about blood vessel shapes such as a blood vessel core line and a blood vessel contour point on a blood vessel orthogonal cross section and correcting blood vessel torsion based on the collected information.

Utilizing such a technique for computerized image diagnosis, it is hoped that abnormalities such as a stenosis can be automatically detected also for the spinal canal.

CITATION LIST

Patent Literature

PTL 1: JP-A-2006-167287

SUMMARY OF INVENTION

Technical Problem

However, it is difficult to apply an evaluation method for the blood vessel stenosis to the spinal canal as is. The reason is because the spinal canal region does not always appear as a closed space in a CT image etc. This is because the spine is comprised of a series of multiple vertebrae and each vertebra shape is also complicated. On the other hand, when evaluating a blood vessel, a blood vessel orthogonal cross section forms a closed space in every cross section. Therefore, although all the cross sections of a blood vessel may be specified as an analysis target, a spine cross section appropriate for evaluating the spinal canal needs to be first identified from among images in which the spine was scanned.

The present invention was made in light of the above problems, and the purpose is to provide an image processing device and a spinal canal evaluation method that can identify a cross-sectional position for evaluating the spinal canal stenosis based on a vertebral region shape on an image and evaluate the spinal canal stenosis in the identified position.

Solution to Problem

In order to achieve the above described purpose, the first invention is an image processing device comprising an extraction unit extracting a vertebral region from a series of tomographic images in which at least a part of the spine was scanned; a calculation unit calculating a length in the anteroposterior direction of an object for each cross section in the vertebral region extracted by the extraction unit; a cross-section identifying unit identifying a cross section including a spinous process if the calculated length in the anteroposterior direction of an object in the vertebral region is larger than a predetermined reference value; a spinal canal stenosis evaluation unit evaluating the spinal canal stenosis by specifying a cross-sectional position identified by the cross-section identifying unit as a site to be analyzed; and a display unit displaying evaluation results by the spinal canal stenosis evaluation unit.

The second invention is the spinal canal evaluation method that evaluates the spinal canal stenosis using a computer, including an extraction step of extracting a vertebral region from a series of tomographic images in which at least a part of the spine was scanned; a calculation step of calculating a length in the anteroposterior direction of an object for each cross section in the extracted vertebral region; an identification step of identifying a cross section including a spinous process if the calculated length in the anteroposterior direction of an object in the vertebral region is larger than a predetermined reference value; an evaluation step of evaluating the spinal canal stenosis by specifying a cross-sectional position identified in the step of identifying a cross section as a site to be analyzed; and a display step of displaying evaluation results in the evaluation step.

Advantageous Effects of Invention

The image processing device and the spinal canal evaluation method of the present invention can particularly identify an image including a spinous process as an analysis target for the spinal canal based on a shape on a vertebral region image and evaluate the spinal canal stenosis in the identified position.

BRIEF DESCRIPTION OF DRAWINGS

FIG. 4 is an explanatory diagram of an extraction region at each stage in vertebral region extraction processing of FIG. 3.

FIG. 5 is a typical image pattern in an extracted vertebral region.

FIG. 6 is an explanatory diagram of a length in the anteroposterior direction of an object in a vertebral region for each image pattern shown in FIG. 5.

FIG. 7 is an explanatory diagram of a method for calculating the length in the anteroposterior direction of an object in a vertebral region.

FIG. 10 is an explanatory diagram of vertebral body separation processing in analysis processing.

FIG. 15 is an example of the evaluation result display window 80a.

FIG. 19 is an explanatory diagram of Steps S403 and S404 in vertebral region extraction processing of FIG. 17.

FIG. 20 is a diagram showing an example where additional lines were drawn in a vertebral image without a closed space to create a closed space.

FIG. 21 is a diagram showing an example where an inscribed ellipse was set for a vertebral image without a closed space as a closed space.

DESCRIPTION OF EMBODIMENTS

Hereinafter, based on diagrams, embodiments of the image processing device and the spinal canal stenosis evaluation method related to the present invention will be described in detail.

[First Embodiment]

First, referring to FIG. 1, the configuration of the image processing system 1 applying the image processing device 100 of the present invention will be described.

Figure 1:
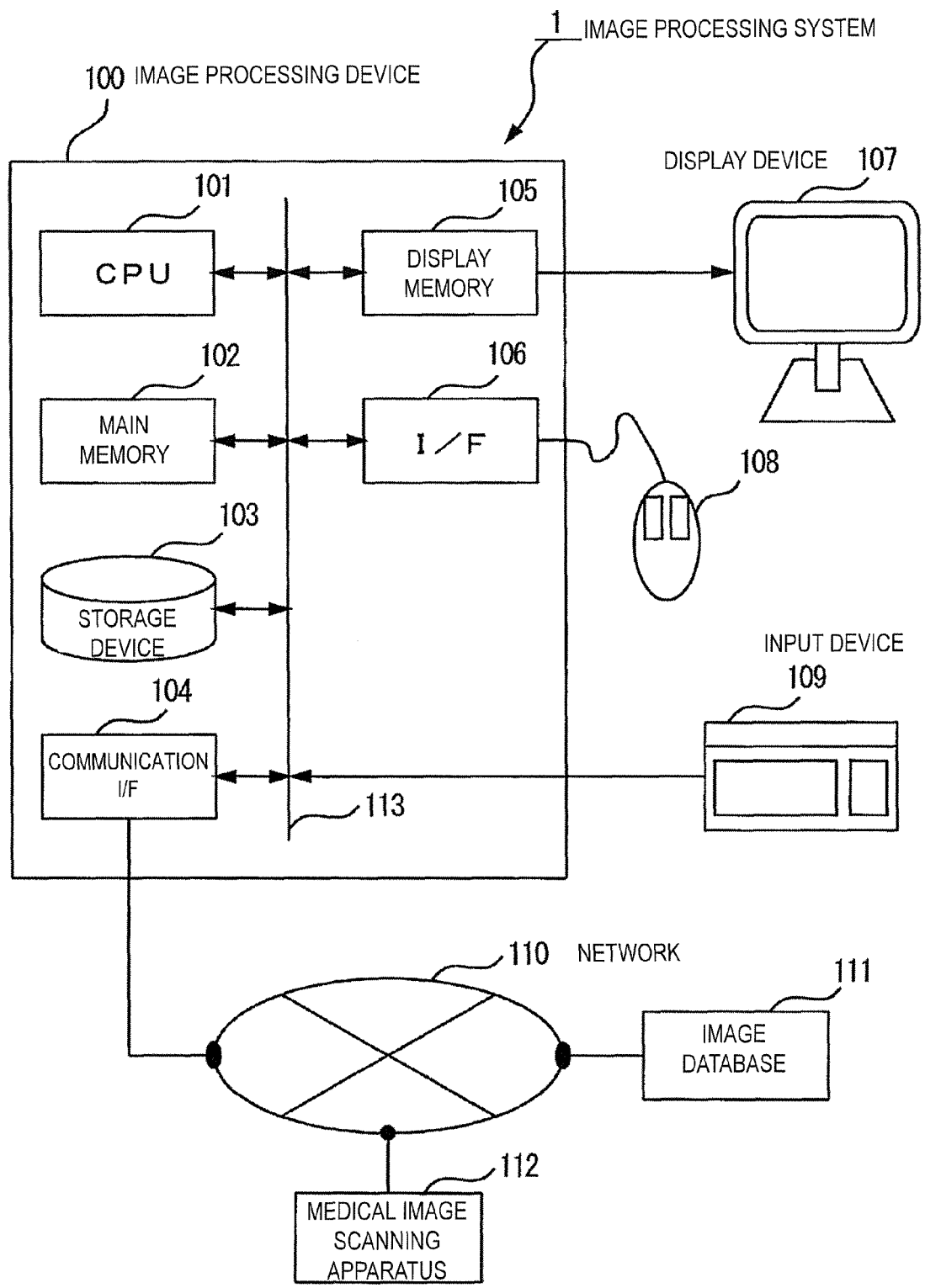
FIG. 1 is a diagram showing the overall configuration of the image processing device 100.

As shown in FIG. 1, the image processing system 1 is comprised of the image processing device 100 having the display device 107 and the input device 109; the image database 111 connected to the image processing device 100 via the network 110; and the medical image scanning apparatus 112.

The image processing device 100 is a computer performing processes such as image generation and image analysis. For example, a medical image scanning apparatus to be installed in a hospital etc. is included.

The image processing device 100 is, as shown in FIG. 1, comprised of the CPU (Central Processing Unit) 101; the main memory 102; the storage device 103; the communication interface (communication I/F) 104; the display memory 105; and the interface (I/F) 106 between external devices such as the mouse 108, and the respective parts are connected via the bus 113.

The CPU 101 executes a program stored in the main memory 102, the storage device103, etc. by loading into a work memory region on a RAM of the main memory 102, drivingly controls the respective parts connected via the bus 113, and achieves various processes to be performed by the image processing device 100.

Also, the CPU 101 performs a process to identify a position to be evaluated for the spinal canal stenosis from a series of tomographic images in which at least a part of the spine of an object was scanned in the spinal canal stenosis evaluation process (see FIG. 2) to be described. Then, based on an image in the identified position, various indexes for evaluating the spinal canal stenosis are calculated, and the evaluation results and images showing a stenosis site are displayed on the display screen. Details for identifying a cross-sectional position to be evaluated for a stenosis and various processes such as calculating an evaluation index of the stenosis will be described later.

The main memory 102 is comprised of a ROM (Read Only Memory), RAM (Random Access Memory), etc. The ROM permanently holds a boot program of a computer, a program such as BIOS, data, etc. Also, the RAM holds a program, data, etc. loaded from the ROM, the storage device 103, etc. temporarily and includes a work memory region to be used for various processes performed by the CPU 101.

The storage device 103 is a storage device reading/writing data to an HDD (Hard Disk Drive) and the other record media as well as stores programs executed by the CPU 101, data required to execute the programs, an OS (Operating System), etc. As the programs, a control program equivalent to an OS and an application program are stored. Each of these program codes is read by the CPU 101 as needed, is moved to the RAM of the main memory 102, and is executed as various means.

The communication I/F 104 has a communication control device, a communication port, etc. and mediates the communication with the medical image processing device 100 and the network 110. Also, the communication I/F 104 performs communication control with the image database 111 and other computers or the medical image scanning apparatus 112 such as an X-ray CT device and an MRI device via the network 110.

The I/F 106 is a port for connecting peripheral equipment and transmits/receives data between the peripheral equipment. For example, a pointing device such as the mouse 108 and a stylus pen may be connected via the I/F 106.

The display memory 105 is a buffer temporarily accumulating display data input from the CPU 101. The accumulated display data is output to the display device 107 at a predetermined timing.

The display device 107 is comprised of a display device such as a liquid crystal panel and a CRT monitor as well as a logic circuit for executing a display process in cooperation with the display device and is connected to the CPU 101 via the display memory 105. The display device 107 displays display data accumulated in the display memory 105 by control of the CPU 101.

The input device 109 is, for example, an input device such as a keyboard and outputs various commands and information input by an operator to the CPU 101. An operator interactively operates the image processing device 100 using external devices such as the display device 107, the input device 109, and the mouse 108.

The network 110 includes various communication networks such as a LAN (Local Area Network), WAN (Wide Area Network), Intranet, and Internet as well as mediates communication connection between the image processing device 100 and the image database 111, a server, the other information devices, etc.

The image database 111 accumulates and stores image data scanned by the medical image scanning apparatus 112. Although the image processing system 1 shown in FIG. 1 has a configuration where the image database 111 is connected to the image processing device 100 via the network 110, the image database 111 may be, for example, provided in the storage device 103 inside the image processing device 100.

Next, referring to FIGS. 2 to 16, the operations of the image processing device 100 in the first embodiment will be described.

Figure 2:
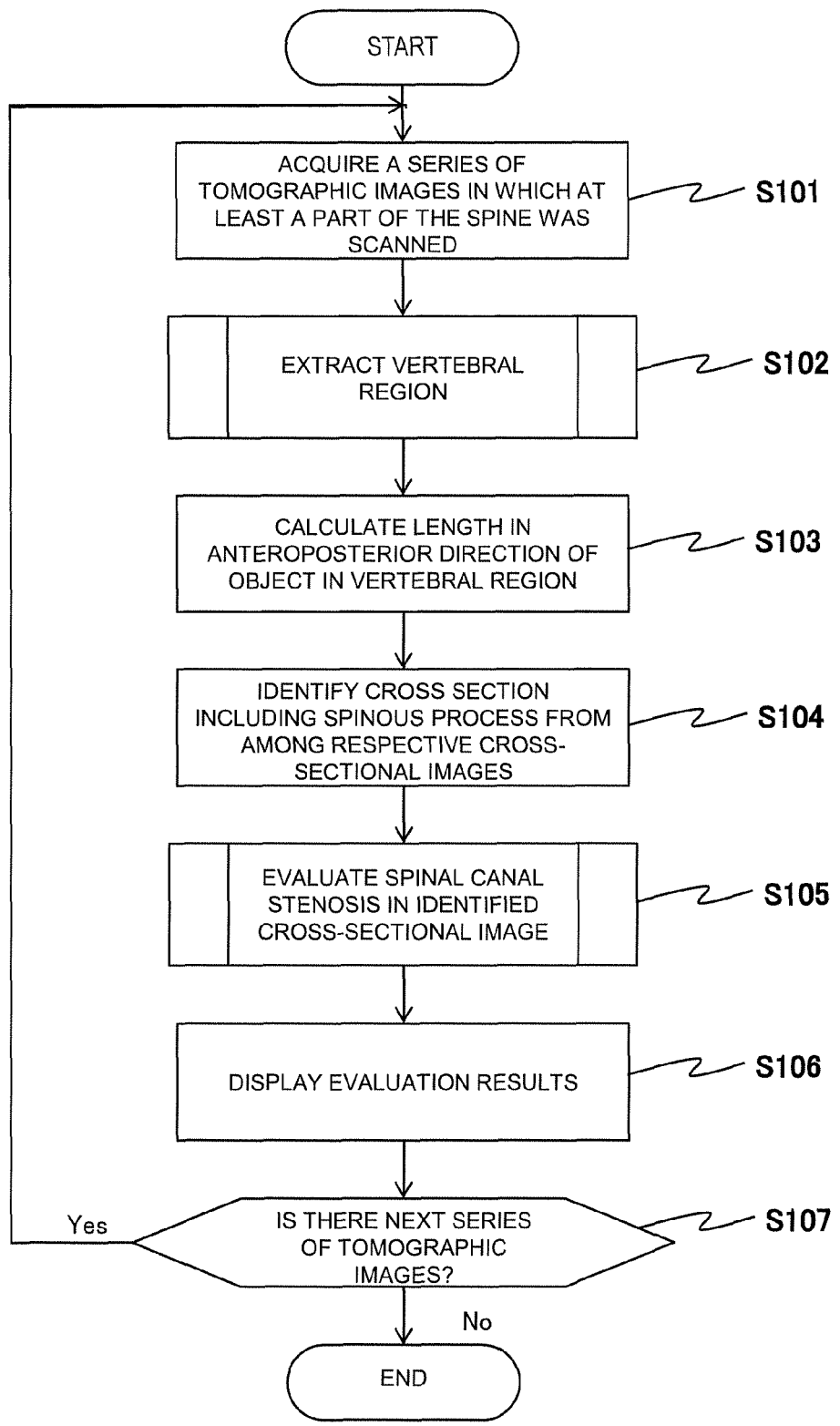
FIG. 2 is a flow chart explaining a flow of the spinal canal stenosis evaluation process executed by the image processing device 100 related to the present invention.

The CPU101 of the image processing device 100 reads out a program and data about the spinal canal stenosis evaluation process in FIG. 2 from the main memory 102 and executes the process based on the program and data.

Additionally, when the execution of the spinal canal stenosis evaluation process is started, data of a series of tomographic images to be calculated is to be fetched from the image database 111 etc. via the network 110 and the communication I/F 104 and is to be stored in the storage device 103 of the image processing device 100.

In the spinal canal stenosis evaluation process of FIG. 2, the CPU101 of the image processing device 100 first reads a series of tomographic images including at least a part of the spine as input image data (Step S101). CT images are suitable as an image to be read.

Here, the spine structure and the characters appearing on a CT image will be described.

The spine is comprised of a plurality of connected vertebrae. That is, the spine has 7 cervical vertebrae, 12 thoracic vertebrae, and 5 lumbar vertebrae that are connected from the head side and has the sacral vertebra and coccyx below. Each vertebra is comprised of a vertebral body, a vertebral foramen, the spinous process, etc. The vertebral body is a cylindrical part located at the front of the vertebra (on the ventral side). The vertebral foramen is a space located behind the vertebral body when looking from the front (ventral side) of an object. Several vertebrae and vertebral foramina are connected, which forms a canal. The canal is referred to as the spinal canal. The spinal cord and the cauda equina nerve run through the spinal canal. A vertebral arch is an arch-shaped part located at the rear of the vertebra (on the dorsal side). Although the vertebral body has a simple shape, the vertebral arch has a complicated shape. The vertebral arch has articular surfaces between the other upper and lower vertebrae, and there are the left and right superior articular processes, inferior articular processes, transverse processes that are centered at the vertebral body, and one spinous process extending to the dorsal side. Between adjacent vertebral bodies, there is an intervertebral disc that is rich in elasticity. Thus, the spine has many gaps. Therefore, a closed space region is small on a CT image.

Figure 3:
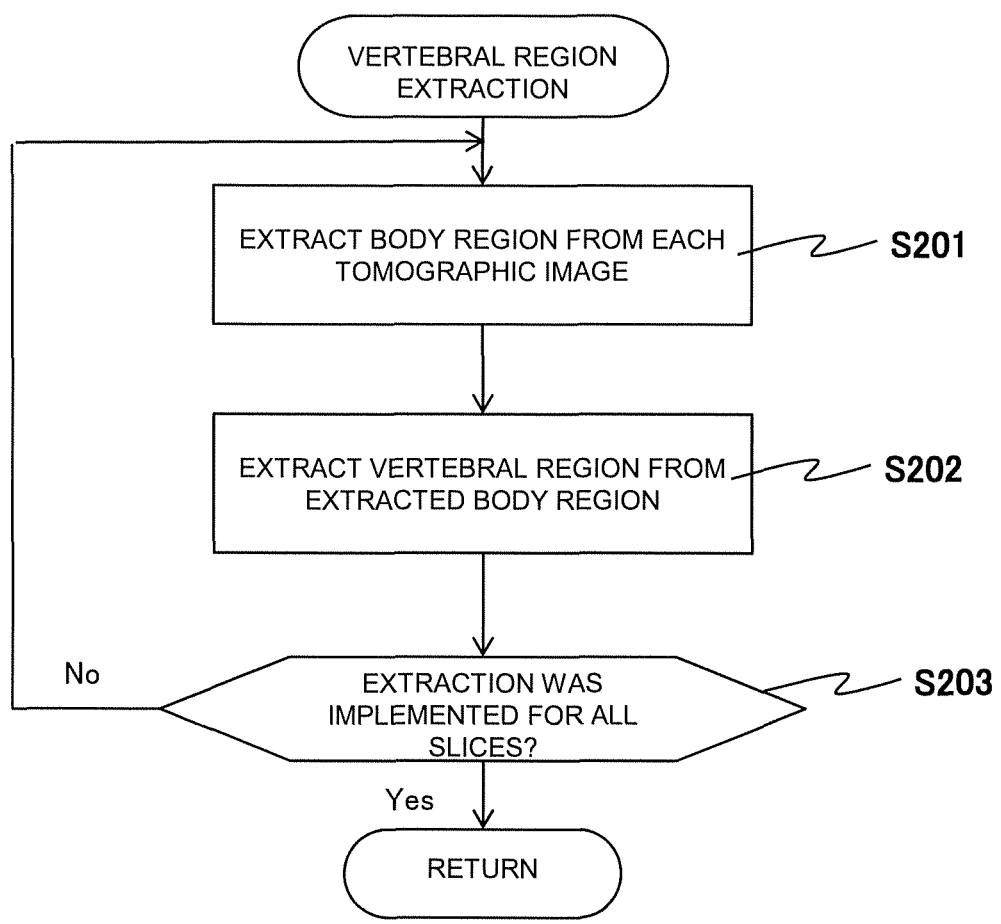
FIG. 3 is a flow chart explaining a flow of vertebral region extraction processing in case of extracting a vertebral region for each slice.

The CPU 101 extracts a vertebral region from a series of tomographic images that was loaded (Step S102). Referring to FIGS. 3 to 5, a process to extract a vertebral region will be described. In the first embodiment, a vertebral region is extracted by specifying an image on a cross section orthogonal to the body axis, i.e. each tomographic image acquired in Step S101 as an image of the extraction source as is.

As shown in the flow chart of FIG. 3, the CPU 101 first extracts a body region from each tomographic image in vertebral region extraction processing (Step S201). The body region extraction is a process to separate an object region from the surrounding area and extract only the object region. The CPU 101 performs a threshold process for each tomographic image to create a binarized image. As the threshold to be used for the threshold process, a predetermined value or a value calculated based on a histogram of a pixel value histogram of the tomographic image may be used.

Next, the CPU 101 performs a labeling process that provides label numbers to discontinuous regions in the created binarized image and extracts a region with the maximum area as a region to be calculated from among the labeled regions. Then, a noise removal process, filling-up process (a process to re-extract pixels that were not extracted despite the pixels should be extracted), etc. are performed as needed to extract as a body region.

Next, the CPU 101 extracts a vertebral region from the extracted body region (Step S202). In vertebral region extraction processing, the CPU 101 first performs threshold processing using an optimal threshold by which the abdominal muscle layer is separated clearly to create a binarized image. The normal CT value of the abdominal muscle layer ranges from "−50" to "100". As described above, a threshold set in advance may be used, and a threshold calculated based on a CT value histogram of a tomographic image may be used. Since the spine locates on the dorsal side than the center of gravity of a body region characteristically, the CPU 101 extracts a muscle region around the spine from a binarized image showing the abdominal muscle layer. FIG. 4(a) is a diagram showing the binarized image 21 at the stage when the abdominal muscle layer was extracted, and FIG. 4(b) is a diagram showing the binarized image 22 at the stage when only a muscle region around the spine was extracted.

The CPU 101 extracts a vertebral region from the extracted muscle region around the spine. The threshold here is set to an optimal threshold by which the bone is separated clearly. Additionally, the normal CT value of the bone ranges from "500" to "1000". Similarly to the above threshold process, the threshold set in advance may be used, and the threshold calculated based on a CT value histogram of a tomographic image may be used. FIG. 4(c) is the image showing a vertebral region 23 extracted from the tomographic image.

When vertebral region extraction for a tomographic image is completed, the CPU 101 determines whether vertebral region extraction processing was performed for all the slices or not (Step S203), and if not, the procedure goes back to Step S201 (Step S203: No). When vertebral region extraction processing is completed for all the slices (Step S203: Yes), the procedure proceeds to Step S103 of FIG. 2.

Here, a typical shape pattern of a vertebral region extracted from a tomographic image will be described by referring to FIG. 5.

The respective images 51, 52, and 53 in FIG. 5 are binarized images of a vertebral region extracted in vertebral region extraction processing of Step S102, in which the pixel value of the bone region is set to "1"; the pixel value of the other region is set to "0, for example. The bone regions are shown with oblique lines in the respective images 51, 52, and 53.

Additionally, a binarized image showing a vertebral region is referred to as a vertebral image (the images 51, 52, and 53 in FIG. 5) in the following descriptions.

As shown in FIG. 5, the vertebral region shape can be changed variously in a CT image. This is caused by that a vertebra has a complicated shape and the spine of a human body is S-shaped so as to connect the respective vertebrae with them inclined.

In the vertebral image 51 of FIG. 5(a), a vertebral body in the upper portion of the image, the vertebral arch in the lower portion of the image (transverse processes and the spinous process), and a closed space showing the spinal canal in the center of the image are found.

Although the vertebral body in the upper portion of the image and a part looking like the spinous process in the lower portion of the image are found in the vertebral image 52 of FIG. 5(b), the center of the image is not a closed space but an open space.

Although the vertebral body in the upper portion of the image and a part looking like the transverse processes of the vertebral arch on the right and left are found in the vertebral image 53 of FIG. 5(c), a part showing the spinous process in the lower portion of the image is not found. Also, although a region showing the spinal canal is found in the center of the image, this region is also an open space, which cannot clearly determine the range of the spinal canal.

Also, although not shown in the diagram, an intervertebral disc between vertebrae is hard to be reflected on a CT image, and if the position is located just in the same position as a cross section, a vertebral body etc. may not also appear clearly in the image.

Thus, in a series of tomographic images in which the spine was scanned, some images are suitable for evaluating the spinal canal stenosis, and others are not suitable. Therefore, the present invention identifies the cross-sectional position appropriate to evaluate the spinal canal stenosis from among the group of these tomographic images.

Hence, the CPU 101 first calculates a length in the anteroposterior direction of an object in a vertebral region extracted from each tomographic image (Step S103 of FIG. 2).

The length in the anteroposterior direction of an object in a vertebral region is a distance between the endpoints on the ventral side and dorsal side on a straight line passing through the center of gravity in a vertebral region. Since the ventral side is toward the upper and the dorsal side is toward the lower normally on a CT tomographic image, the vertical direction of the image corresponds to a direction connected between the ventral side and the dorsal side of an object, i.e. the anteroposterior direction of the object. However, in a case where inclination occurs to vertebrae and a case where an image of an arbitrary cross section is used for the original image of vertebral region extraction, the vertical direction of the image does not necessarily correspond to the anteroposterior direction of the object. In this case, the center of gravity and the inclination of the vertebral region are calculated to determine the principal axis of inertia, and a distance between the endpoints of the vertebral region on the principal axis of inertia should be calculated.

FIG. 6 is an explanatory diagram of a method for calculating a length in the anteroposterior direction of an object in a vertebral region in the respective vertebral images 51, 52, and 53 shown in FIG. 5. In the respective diagrams in FIG. 6, the principal axis of inertia 62 in a vertebral region corresponds to the vertical direction of the images.

As shown in FIG. 6(a), a length of the bidirectional arrow 63a is to be a length in the anteroposterior direction of an object in a vertebral region of the vertebral image 51. That is, a distance between the endpoints on the ventral side and dorsal side on a straight line passing through the center of gravity 61 in the vertebral region is a length in the anteroposterior direction of the object in the vertebral region. Lengths of a vertebral body in the upper portion of the image, the spinous process in the lower portion of the image, and a closed space (spinal canal) in the center of the image are to be included in the length 63a.

As shown in FIG. 6(b), a length of the bidirectional arrow 63b is to be a length in the anteroposterior direction of an object in a vertebral region in the vertebral image 52. Similarly to FIG. 6(a), a distance between the endpoints on the ventral side and dorsal side on a straight line passing through the center of gravity 61 in the vertebral region is a length in the anteroposterior direction of the object in the vertebral region. Lengths of a vertebral body in the upper portion of the image, the spinous process in the lower portion of the image, and a space other than bones (spinal canal) in the center of the image are to be included in the length 63b.

A length of the bidirectional arrow 63c is to be a length in the anteroposterior direction of an object in a vertebral region in the vertebral image 53 shown in FIG. 6(c). No spinous process region is found in the vertebral image 53. Therefore, only a length in the vertebral region in the upper portion of the image is to be included in a distance between the endpoints on the ventral side and the dorsal side on a straight line passing through the center of gravity 61 in the vertebral region.

Additionally, a method for calculating a length in the anteroposterior direction of an object in a vertebral region is not limited to the method for calculating a distance between two points from coordinate values of the respective endpoints on the ventral side and dorsal side as described above, and the other calculation method may be used. For example, a run-length may be calculated. Although a run-length generally means a length (the number of pixels) of a part where the same pixel values continue, the run-length means "a length (the number of pixels) in a region (vertebral region)" in the present specification. In the following description, it is referred to as "fill-up run-length" in order to distinguish from the run-length with a general meaning. For example, in a case where a part other than a bone region is included in a vertebral region as shown in FIGS. 5(a) and 5(b), the fill-up run-length is a length for which the part other than the bone region is converted (filled up) into a pixel value of the bone and is counted as a grouped region.

Specifically, in a vertebral region having a closed space inside as shown in FIG. 6(a), a pixel value on a straight line (the principal axis of inertia 62) passing through the center of gravity and connecting the ventral side and dorsal side includes a part of "1", "0", and "1". That is, there is the region other than bones 65 inside a bone region. In this case, as shown in FIG. 7(a), the CPU 101 counts the number of pixels while performing the fill-up process (converting the pixel value "0" into "1") for pixels from the endpoint on the ventral side to the endpoint on the dorsal side in the vertebral region. The count value is referred to as a fill-up run-length RL.

Even in a vertebral region having an open space in the center as shown in FIG. 6(b), the CPU 101 similarly counts the number of pixels while performing the fill-up process (converting the pixel value "0" into "1") for pixels from the endpoint on the ventral side to the endpoint on the dorsal side in the vertebral region in order to calculate a fill-up run-length.

In a vertebral region without the spinous process as shown in FIG. 6(c), the pixel value on the principal axis of inertia 62 is "1" and "0" from the end. That is, the region of the pixel value "0" is not sandwiched between the regions of the pixel value "1". In this case, the number of pixels is counted only in the region of the pixel value "1", and the count value is referred to as a run-length in the vertebral region.

Also, as shown in FIG. 7(b), the run-lengths RL1 and RL2 (lengths of the pixel values "1" continue) in the general sense are calculated respectively in a bone region on the principal axis of inertia, and the sum of these (RL1+RL2) may be specified as a length in the anteroposterior direction of an object in a vertebral region.

Thus, the CPU 101 calculates lengths in the anteroposterior direction of an object in a vertebral region for all the cross sections (tomographic images) using a distance between two points, a fill-up run-length, the sum of run-lengths, etc. described above. Then, based on the calculated lengths in the anteroposterior direction of an object in a vertebral region, cross sections including spinous processes are identified (Step S104 of FIG. 2).

The cross section identification process in Step S104 of FIG. 2 will be described by referring to FIG. 8.

Figure 8:
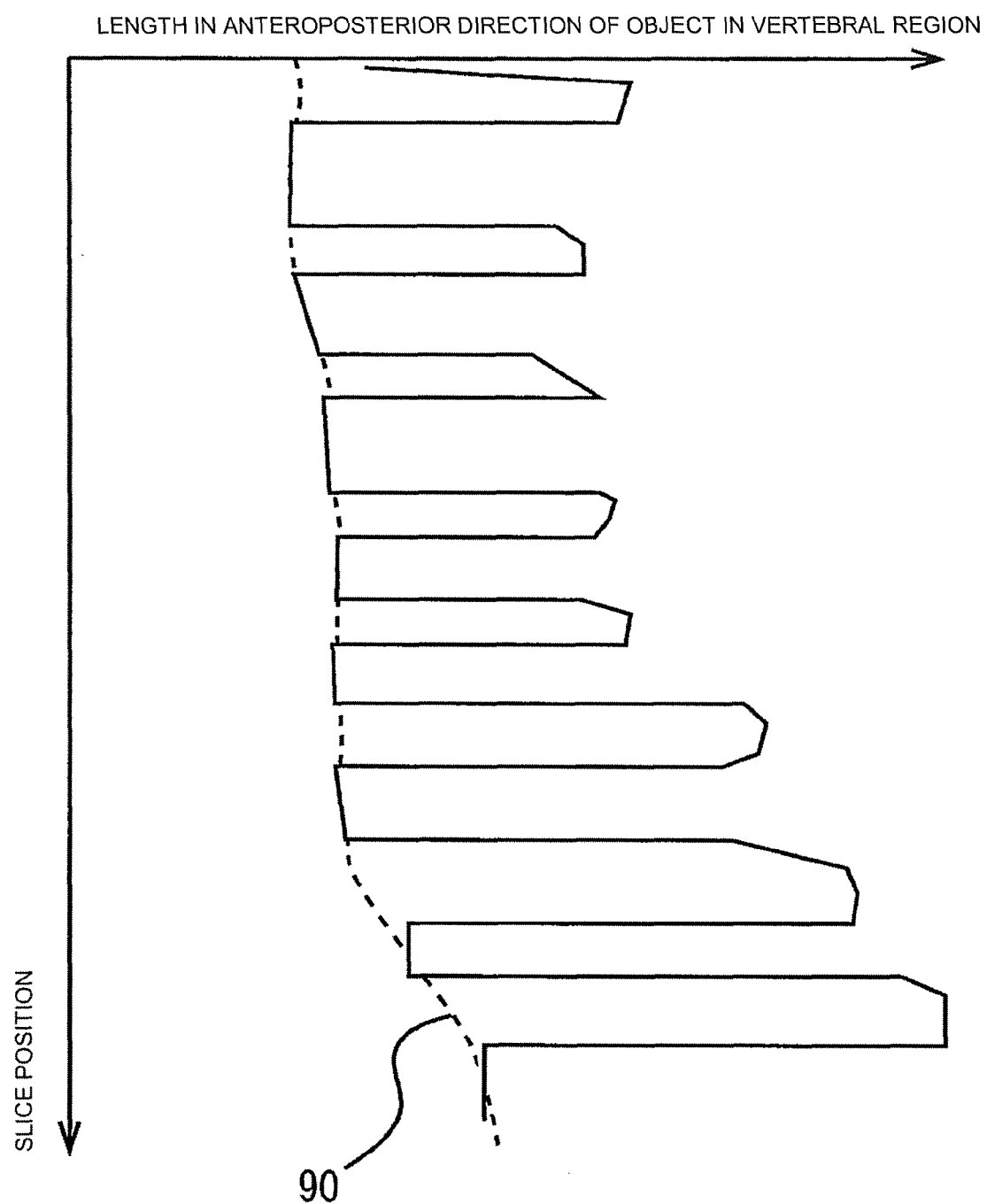
FIG. 8 is a graph where lengths in the anteroposterior direction of an object in a vertebral region on each cross section are arranged in the slice direction.

In the graph of FIG. 8, the vertical axis represents a slice position, and the horizontal axis represents a length in the anteroposterior direction of an object in a vertebral region that calculated in Step S103. The length in the anteroposterior direction of an object in a vertebral region may be specified using any value of a distance between two points, a fill-up run-length, and the sum of run-lengths described above. Also, the broken line 90 shown in FIG. 8 is a reference curve for determining the presence or absence of the spinous process.

For the lengths in the anteroposterior direction of an object in a vertebral region that was calculated in Step S103, when checking the lengths in slice positions, there is a slice position where the length protrudes locally as shown in FIG. 8. This means that a length in the anteroposterior direction of an object in a vertebral region conspicuously protrudes in a slice position including a spinous process and shortens in the other slice positions. By utilizing such characteristics, the CPU 101 identifies a slice position where a length in the anteroposterior direction of an object in a vertebral region is larger than a predetermined reference value as a cross section including a spinous process.

Additionally, a reference value for determining whether to be a cross section including a spinous process or not is set to an average value of all the slices of lengths in the anteroposterior direction of an object in a vertebral region, for example. Alternatively, a curve (the broken line 90 in FIG. 8) showing a standard length of a vertebral body using the rolling ball method, the higher-order spline interpolation, etc. is calculated, and the calculated curve may be specified as a reference value (reference curve). The rolling ball method is a method for determining a curve based on a trajectory drawn by the outer surface of the ball with a predetermined diameter when virtually rolling the ball along a graph.

Also, since vertebral body sizes vary depending on the site (cervix, thorax, lumbar, etc.), a half of the maximum value of a length in the anteroposterior direction of an object in a vertebral region may be set to a reference value. In this case, the reference value is to be set lower than the above average value, which can prevent cross-sectional identification from being omitted.

After a cross section including a spinous process is identified by the process of Step S104, the CPU 101 next analyzes the spinal canal based on the identified cross-sectional tomographic image to evaluate the stenosis (Step S105 of FIG. 2).

The spinal canal analysis process in Step S105 of FIG. 2 will be described by referring to FIG. 9.

Figure 9:
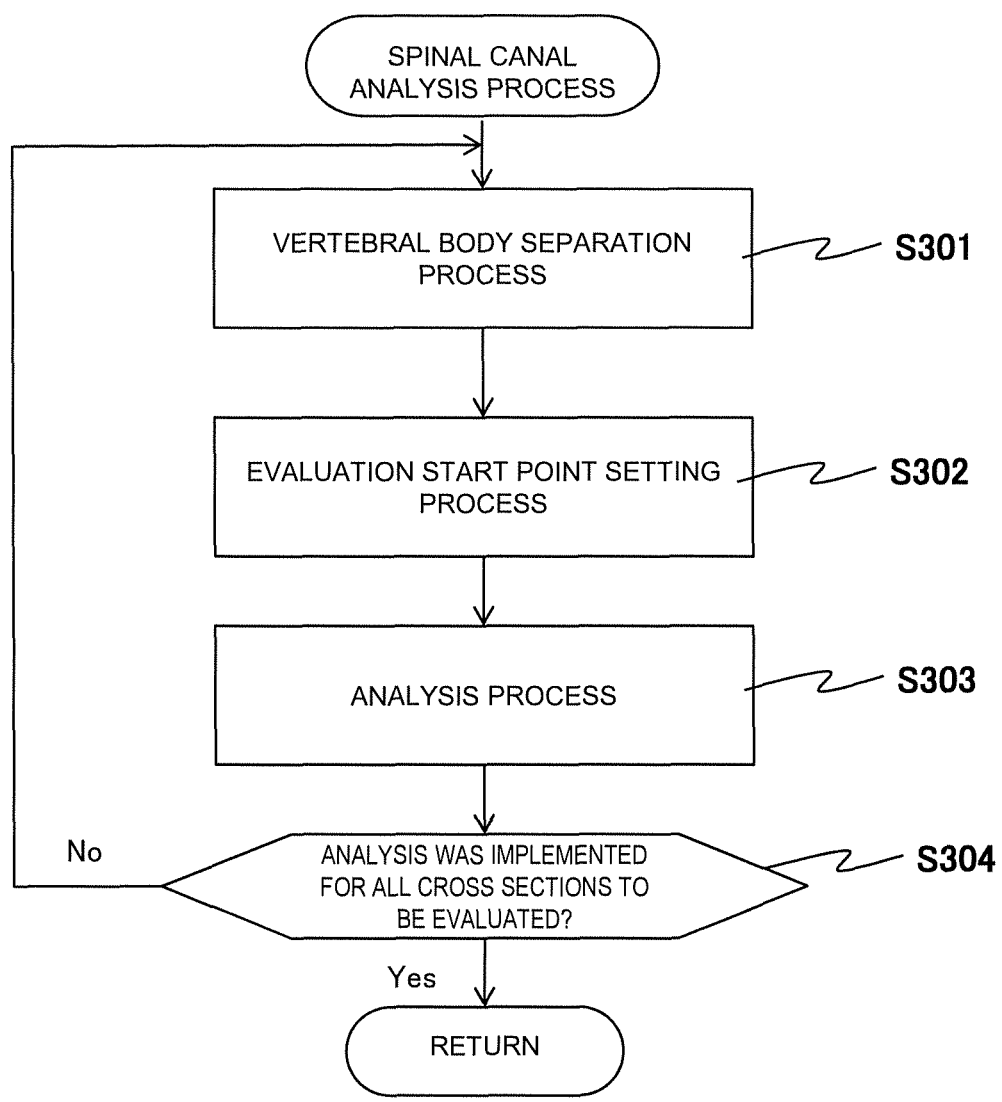
FIG. 9 is a flow chart explaining a flow of spinal canal analysis processing.

In the spinal canal analysis process shown in FIG. 9, an asymmetry of a spinal canal shape on a cross section to be analyzed is calculated as an evaluation index.

When the asymmetry of the cross section shape of the spinal canal is evaluated, for example, a distance between a vertebral body and a vertebral arch in each position where the left and right distances from the center of gravity in a vertebral region are the same, i.e. a thickness of the spinal canal is calculated to evaluate the difference between the left and right.

Therefore, the CPU 101 first performs a process to separate a vertebral body from a vertebral arch on a cross section including a closed space in a vertebral region from among cross sections (those including spinous processes identified in Step S104) to be analyzed (Step S301).

For example, as shown in the vertebral image 51 of FIG. 10(a), the CPU 101 performs the vertebral-body separation process in Step S301 for a vertebral region having a closed space inside. Because a vertebral region is already separated in the vertebral image 52 shown in FIG. 5(b), the separation process in Step S301 may not be performed.

In the vertebral-body separation process in Step S301, the CPU 101 scans a vertebral region in the up-and-down direction (vertical direction) of an image by setting the center of gravity 61 in the vertebral region as a search starting point to identify the spinal canal region. The spinal canal region is a region (closed space) other than bones inside the vertebral region. Then, the CPU 101 sets the separation line 67 for a bone region (vertebral body) on the side upper than the top of the spinal canal region.

Specifically, for example, in the vertebral image 51 including a vertebral region with a shape shown in FIG. 10(a), the space of the pixel value "0" surrounding the center of gravity 61 in the vertebral region is referred to as the spinal canal region 40 as shown in FIG. 10(b). Then, an ellipse similar to a bone region (vertebral body) shape on the upper of the spinal canal region 40 is calculated. That is, the ellipse is set by specifying a distance from the top point 41 in the spinal canal region 40 to the end point 42 on the ventral side (upper side) in the upper vertebral-body region as the short diameter a1 and the longest width in the horizontal direction in the vertebral region upper than the top point 41 as the long diameter b1. The line showing the ellipse and coming into contact with the bone region is referred to as the separation line 67.

Additionally, the vertebral-body separation process is not limited to the ellipse approximation method, and the other method may be used.

For example, a smooth curve connecting the top point 41 in the spinal canal region to the curves on the edges of a vertebral body (the upper portion of a vertebral region) is calculated by higher-order curve approximation, and the curve may be referred to as the separation line 67.

Next, the CPU 101 sets an evaluation start point P and a search range (Step S302). The evaluation start point P is set to the central lowest end point in the spinal canal region 40, for example. The CPU 101 scans a vertebral region in the upper (vertical) direction of an image from the lowest end point of the spinous process and sets a point whose pixel value is 0, i.e. the central lowest end point in the spinal canal region as an evaluation start point P. Also, for example, as shown in the straight lines Le and Re of FIG. 11, a width of a closed space should be set as a search range in a case where the spinal canal region is the closed space.

Figure 12:
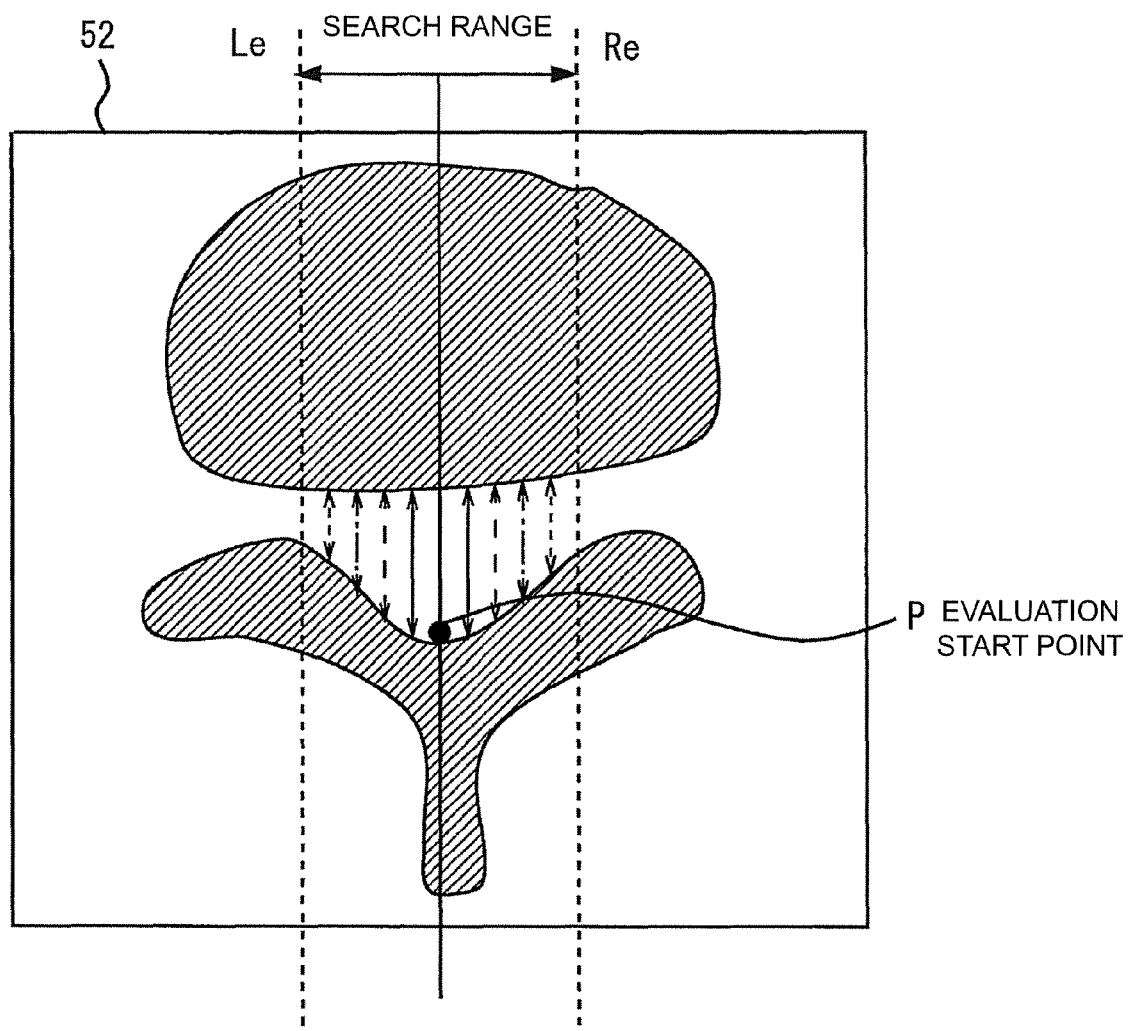
FIG. 12 is an example of calculating an evaluation index of the spinal canal for a vertebral image where a closed space does not exist.

Also, as shown in FIG. 12, in a case where the spinal canal region is an open space, a range where a distance between the bone region (upper side) on the vertebral body side and the bone region (lower side) on the spinous process side is larger than a predetermined value should be set as a search range.

Figure 11:
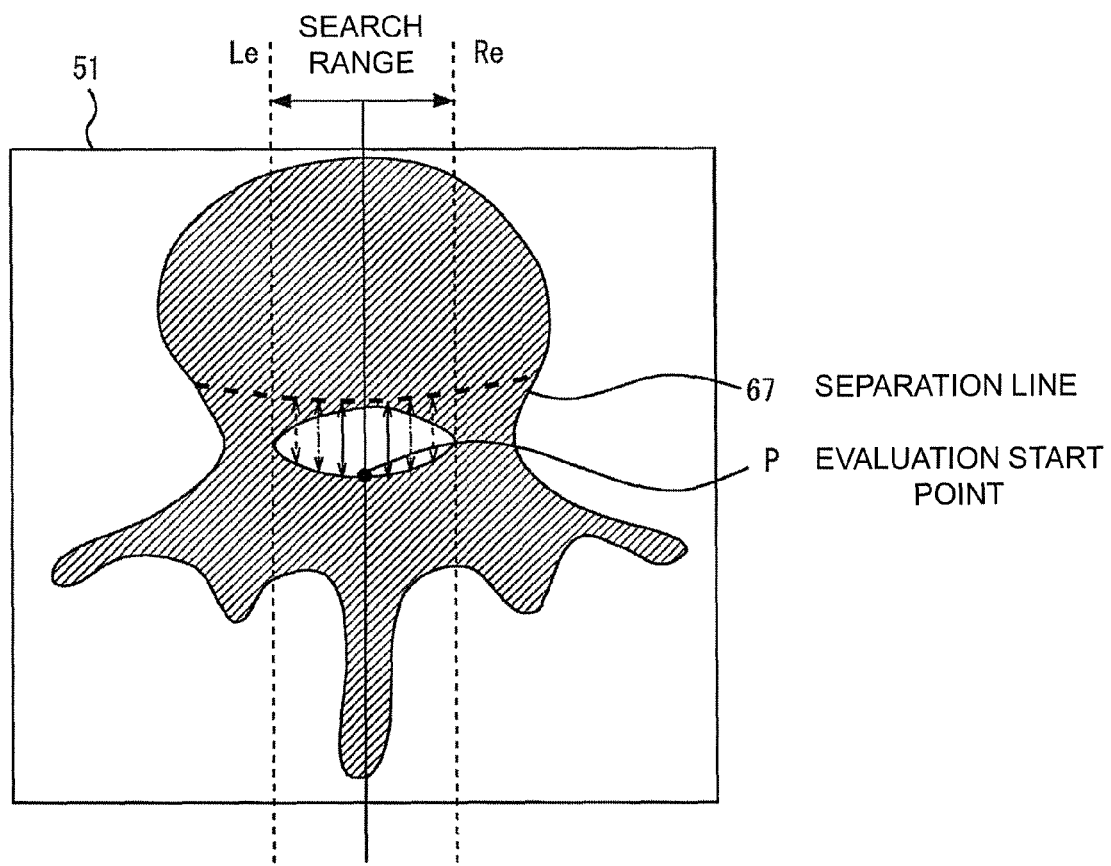
FIG. 11 is an example of calculating an evaluation index of the spinal canal for a vertebral image including a closed space.

After the evaluation start point P and the search range are set, the CPU 101 executes an analysis process (Step S303). In the analysis process in Step S303, the CPU 101 first measures and compares thicknesses of the spinal canal in each position where the left and right distances are the same with the evaluation start point P set as the starting point. For example, as shown in the arrows of FIGS. 11 and 12, the thicknesses of the spinal canal are distances in the vertical direction of the image from the bottom portion of the spinal canal to the bottom portion of the vertebral body (the separation line 67 in FIG. 11). The CPU 101 compares the calculated distances with each other in the positions where the left and right distances from the evaluation start point P are the same.

In the examples of FIGS. 11 and 12, thicknesses of the spinal canal (arrow length) are compared with each other in the positions where the left and right distances are the same as shown in the respective arrows (solid-line arrows, dot-dashed-line arrows, and broken-line arrows) disposed in the positions where the left and right distances from the evaluation start point P are the same. If the left and right thicknesses of the spinal canal in the positions where the left and right distances from the evaluation start point P are the same vary at a predetermined rate or more, it is presumed that a part of the vertebral arch or the vertebral body is being pressed.

Then, the CPU 101 calculates a ratio showing how different the left and right thicknesses of the spinal canal are as an evaluation index. Alternatively, areas in the left and right regions of the spinal canal may be calculated by setting the center line drawn from the evaluation start point P as a boundary to calculate the area ratio as an evaluation index.

Figure 13:
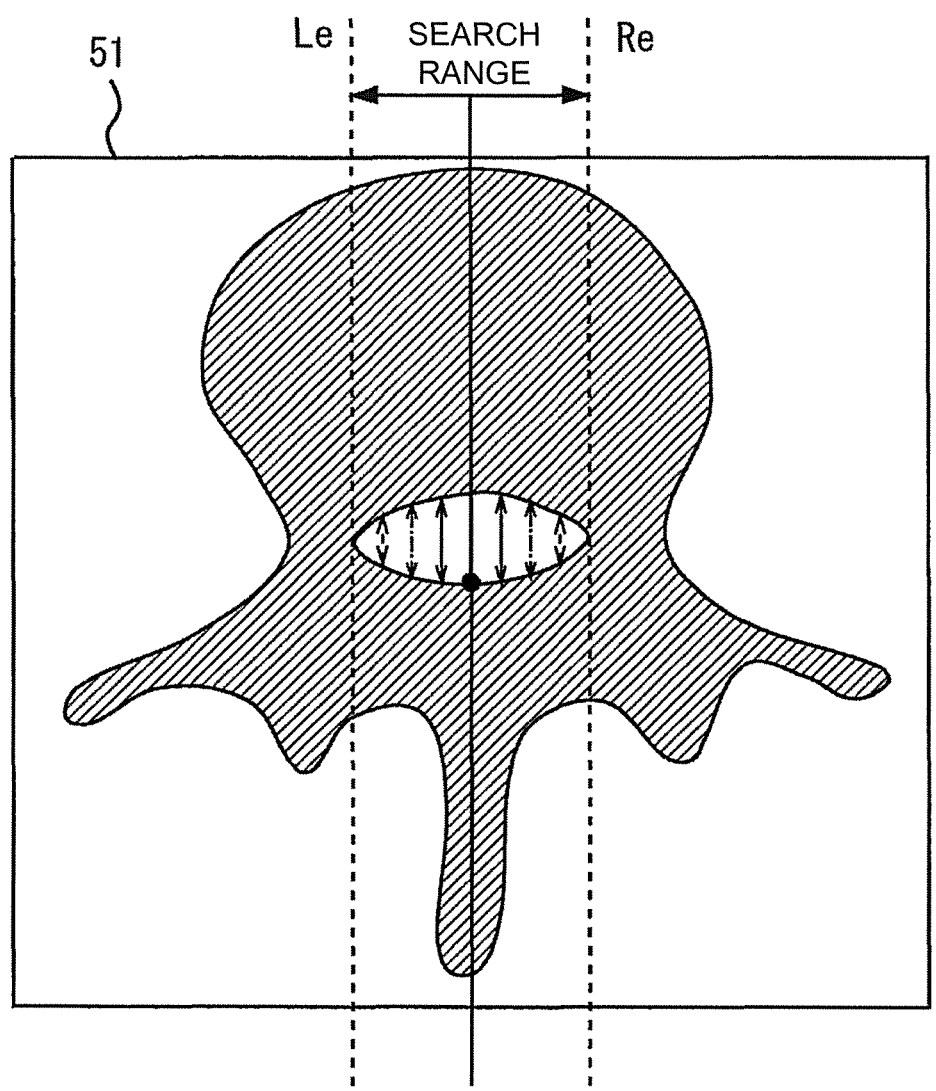
FIG. 13 is another example of calculating an evaluation index of the spinal canal for a vertebral image including a closed space.

Also, in the vertebral image 51 where the spinal canal region is shown as a closed space, the distances in the vertical direction may be calculated inside the closed space without setting the separation line 67 to compare them with each other in each position where the left and right distances from the evaluation start point P are the same, as shown in FIG. 13.

Thus, when the evaluation index calculation is completed in Step S303, the CPU 101 determines whether all the cross-sections to be evaluated were analyzed or not (Step S304), and if any cross section to be evaluated has not been analyzed yet (Step S304: No), the processes from Step S301 to Step S303 are repeated.

If all the cross-sections to be evaluated have been analyzed (Step S304: Yes), the procedure proceeds to Step S106 of FIG. 2.

Figure 14:
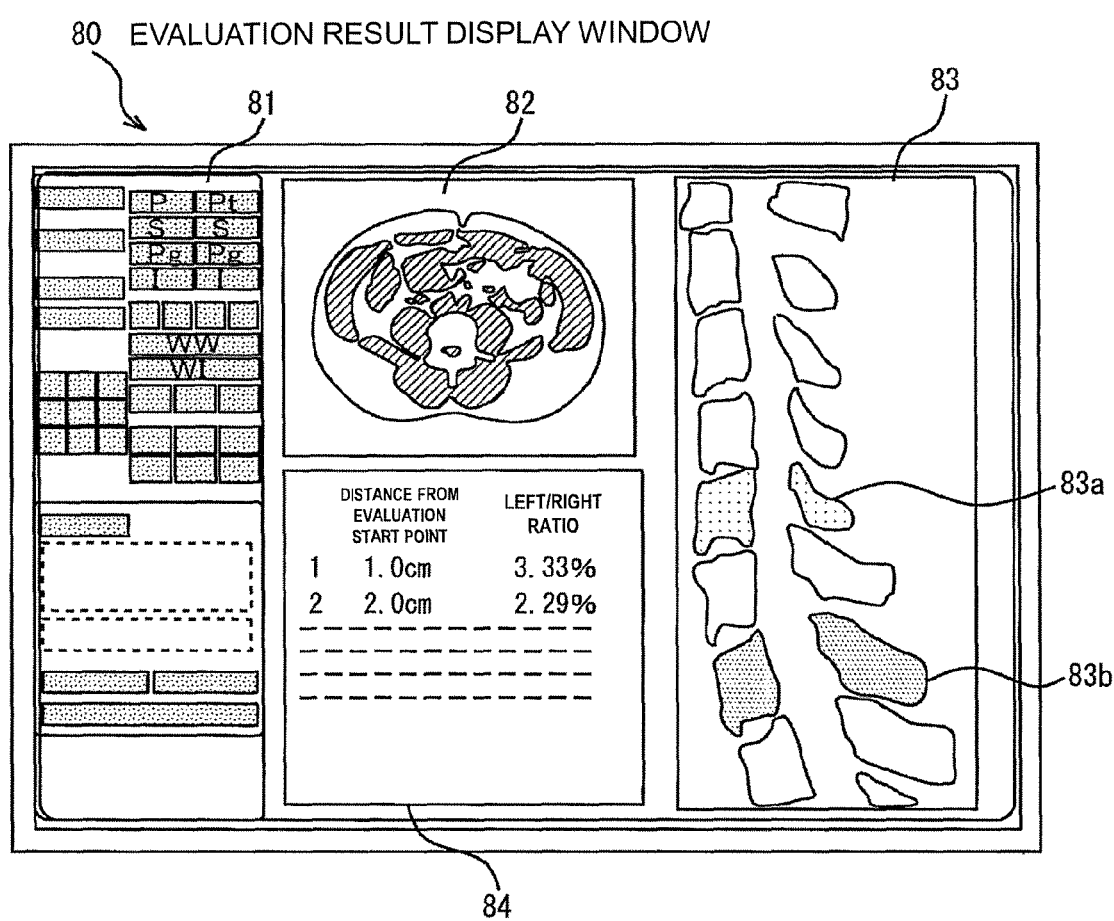
FIG. 14 is an example of the evaluation result display window 80.
Figure 15:
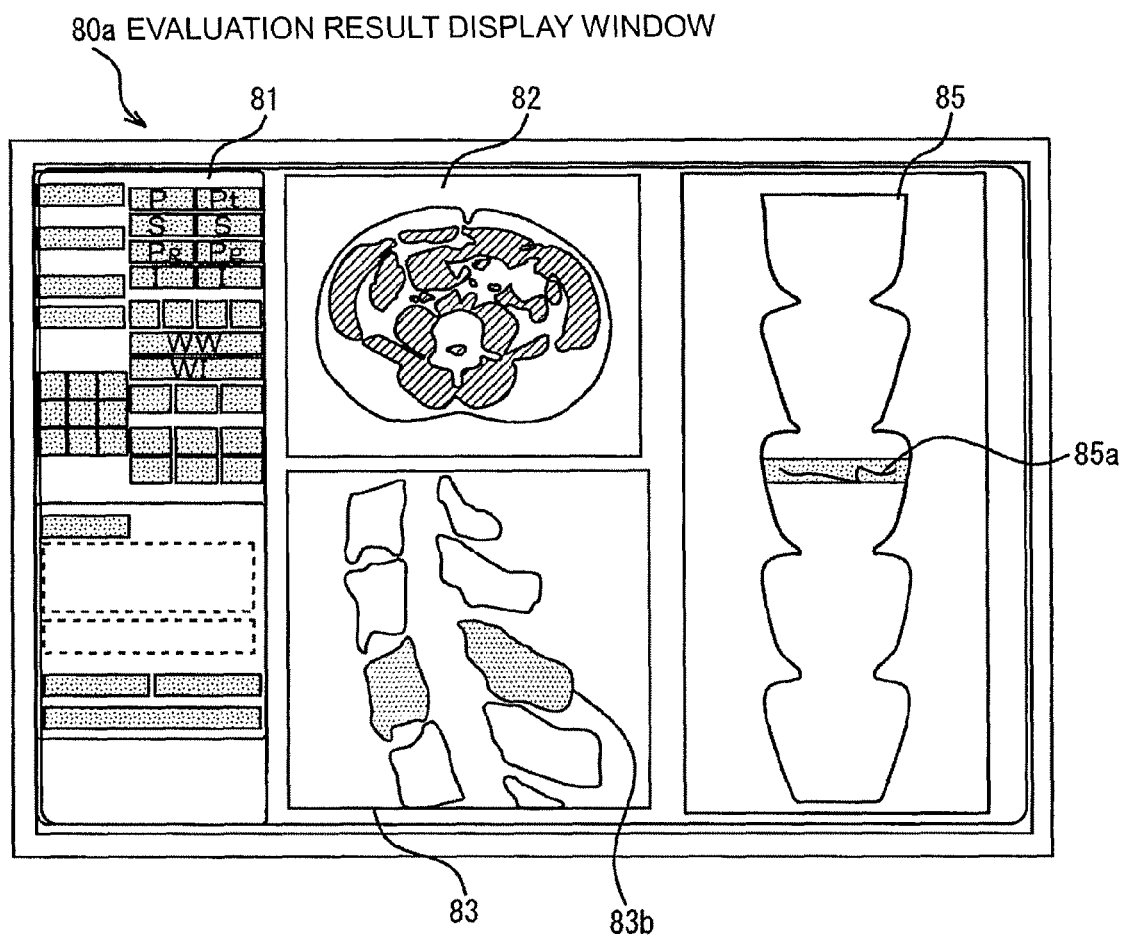
Figure 16:
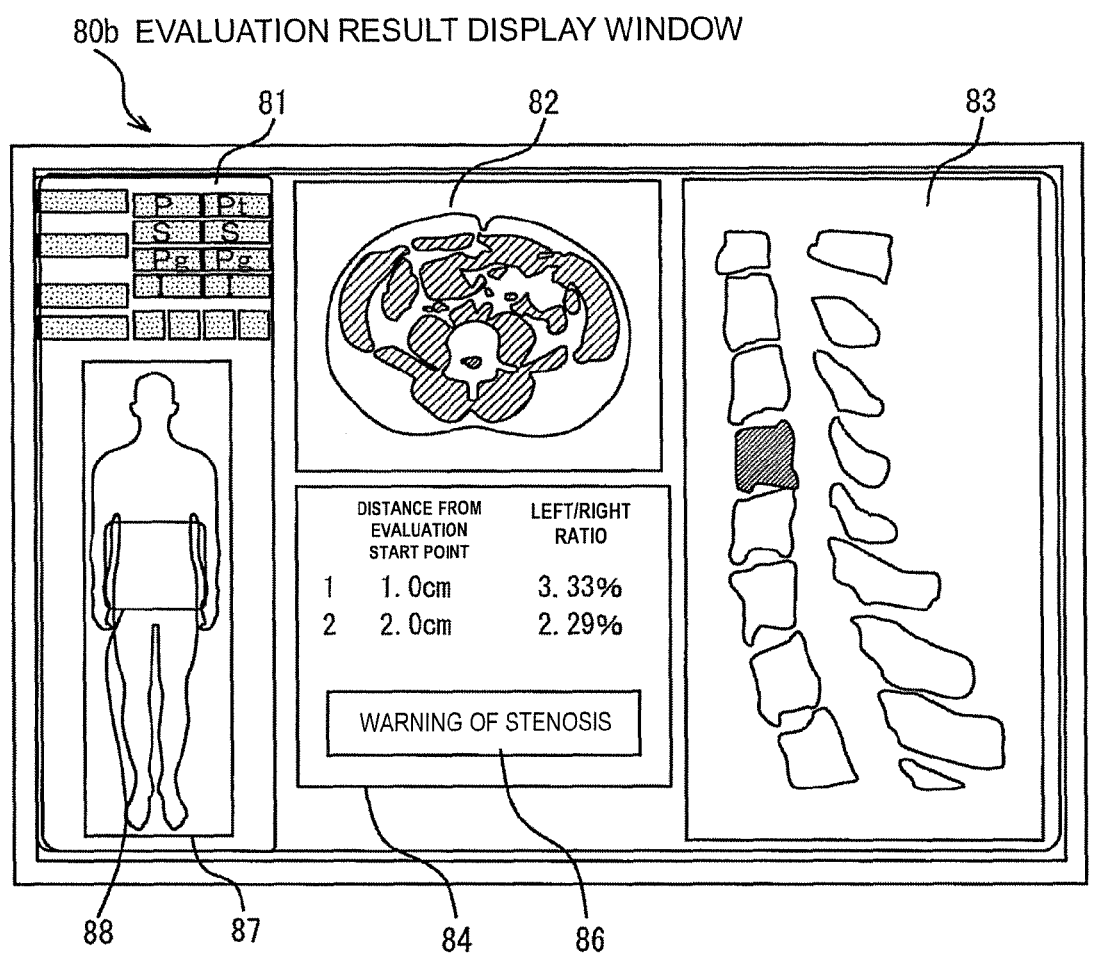
FIG. 16 is an example of the evaluation result display window 80b.

In Step S106 of FIG. 2, the CPU 101 displays evaluation results of Step S105 (the spinal canal analysis process of FIG. 9) (Step S106). FIGS. 14 to 16 are diagrams showing display examples of the evaluation results.

On the evaluation result display window 80 shown in FIG. 14, the operation input area 81, the evaluation target image display area 82, the spine image display area 83, the evaluation result list display area 84, etc. are provided.

In the operation input area 81, the buttons, keys, input fields, etc. to input various operations related to image analysis are provided. For example, a forward button to specify an image to be processed, an input field to input a threshold to be used for binarization processing, a button to adjust a size of an image to be displayed and a CT value range, a button to adjust the other various parameters, etc. are provided.

In the evaluation target image display area 82, a tomographic image specified in the operation input area 81, an image to be processed, etc. are displayed.

A spine image showing at least a part of the spine is displayed in the spine image display area 83. For example, the spine image to be displayed may be a sagittal image in which the vertical axis is in the body-axis direction of an object and the horizontal axis is in the anteroposterior direction of an object or may be a CPR (Curved Planar Reconstruction) image in which a plane along the spine is a cross section. In the example of FIG. 14, a spine sagittal image in which the vertical direction is in the body-axis direction of an object and the horizontal direction is in the anteroposterior direction of an object is displayed.

Also, from among the respective vertebrae in a spine image, the vertebrae 83a and 83b in which abnormalities such as a stenosis were detected may be displayed by emphasizing them with colors, marks, etc.

The evaluation result list display area 84 displays an evaluation result list showing evaluation results of the spinal canal stenosis in a cross section with numerical values. For example, the evaluation result list for the cross section displayed in the evaluation target image display area 82 is displayed. In the example shown in FIG. 14, from among ratios of the left and right thicknesses of the spinal canal in the respective points where the left and right distances from the evaluation start point P are the same, the ratios with higher values are shown in order in the evaluation result list. Specifically, it is described that the "3.33%" difference in the spinal canal thickness is caused in the position 1 cm away from the evaluation start point P to the left and right; and the "2.29%" difference in the spinal canal thickness is caused in the position 2 cm away from the evaluation start point P to the left and right in the list.

When an arbitrary vertebra is selected by a mouse etc. in a spine image displayed in the spine image display area 83, the CPU 101 may be configured so that an image (tomographic image) including the vertebra is displayed in the evaluation target image display area 82. Also, it may be configured so that evaluation results of the spinal canal stenosis in the tomographic image are displayed in the evaluation result list display area 84.

Additionally, the contents of the evaluation result list of FIG. 14 is an example, and various evaluation indexes analyzed in the spinal canal analysis process (FIG. 9) and contents according to the evaluation results are displayed.

Also, as shown in the evaluation result display window 80a FIG. 15, it may be configured so that an unfolded image of the spinal canal region is displayed.

In the evaluation result display window 80a shown in FIG. 15, the operation input area 81, the evaluation target image display area 82, the spine image display area 83, the unfolded image display area 85, etc. are provided. Although the layout position of the spine image display area 83 is different from the evaluation result display window 80 of FIG. 14, the display contents of the operation input area 81, the evaluation target image display area 82, and the spine image display area 83 are similar to the evaluation result display window 80 of FIG. 14.

In the evaluation result display window 80a of FIG. 15, an unfolded image of the spine (spinal canal) is displayed in the unfolded image display area 85. The unfolded image is an image in which the spinal canal is cut and opened virtually in the longitudinal direction to project pixel values at each point inside the canal to each corresponding point on the plane. By displaying the unfolded image, a calcification state etc. inside the spinal canal can be visually recognized. Also, for a site with abnormalities such as a stenosis, the corresponding vertebra 83b in a spine image in the spine image display area 83 and the corresponding site 85a in an unfolded image in the unfolded image display area 85 may be highlighted.

Also, as shown in the evaluation result display window 80b of FIG. 16, the entire image 87 of an object is displayed, and the range 88 displayed in the spine image display area 83 may be shown on the entire image 87. The entire image 87 may be a scanogram image obtained during CT scanning, a standard human-body illustration, etc.

Also, in the evaluation result list display area 84, the alert display 86 showing that there are abnormalities such as a stenosis may be further displayed together with an evaluation result list.

After displaying the evaluation results of the spinal canal stenosis, the CPU 101 determines whether there is the next series of tomographic images or not (Step S107 of FIG. 2), and if there is the next series of tomographic images (Step S107: Yes), the CPU 101 goes back to Step S101 to repeat the processes from Step S101 to Step S106 for the next series of tomographic images.

If there is not the next series of tomographic images (Step S107: No), the spinal canal stenosis evaluation process is completed.

As described above, the image processing device 100 of the first embodiment extracts a vertebral region from a series of tomographic images in which at least a part of the spine was scanned, calculates a length in the anteroposterior direction of an object for each cross section in the vertebral region, identifies a cross section including a spinous process based on the length in the anteroposterior direction of an object in the calculated vertebral region, evaluates the spinal canal stenosis by specifying the identified cross-sectional position as a site to be analyzed, and then displays the evaluation results.

Hence, calculation can be executed for the spinal canal region of various shapes on an image by excluding a cross section inappropriate for evaluation from processing targets, which can evaluate the spinal canal stenosis using a computer such as the image processing device 100.

Also, stenosis evaluation can be performed in a spinal canal region where a closed space hardly appears on an image because of many gaps and various shapes are formed.

Also, in a cross section to be analyzed, if there is a closed space showing the spinal canal inside an extracted vertebral region, the spinal canal stenosis is evaluated based on the closed space shape. Alternatively, a separation line is set in a position estimated to be the edge on the spinal canal side of a vertebral body to compare distances between the separation line and a vertebral arch in the positions where the left and right distances from the center of the spinal canal are the same. This results in that an inequality between the left and right thicknesses of the spinal canal in a cross section to be analyzed can be evaluated.

In an evaluation result display window, a spine image showing the spine in the body-axis direction is displayed, and a vertebra that was determined to have a stenosis is distinguishably displayed. Additionally, an unfolded image of the spinal canal is displayed, and a site that was determined to have a stenosis may be distinguishably displayed also in the unfolded image. Also, the evaluation results may be listed and displayed, and an alert may be displayed in case of detecting abnormalities such as a stenosis.

Hence, this results in that the spinal canal stenosis can be automatically evaluated using a computer based on a group of tomographic images such as CT images to present the evaluation results. Particularly, because a cross section for evaluation is identified to be a cross section where the spinous process is included, the evaluation results can be obtained efficiently by excluding images inappropriate for evaluation.

[Second Embodiment]

Next, referring to FIGS. 17 to 19, the second embodiment of the present invention will be described.

In the first embodiment, a vertebral region is extracted from the respective tomographic images orthogonal to the body axis, and a cross-sectional position to evaluate the spinal canal stenosis is identified based on a length in the anteroposterior direction of an object in an extracted vertebral region. However, since the spine is S-shaped, the respective vertebrae are connected with a certain degree of inclination. Therefore, in a case where a vertebral region is extracted from the respective tomographic images orthogonal to the body axis, the inclination degree of the vertebral bodies may be an angle difficult to evaluate the spinal canal stenosis.

Therefore, in the second embodiment, a vertebral cross-sectional image orthogonal to each vertebral body is generated, and a vertebral region is extracted from the generated vertebral cross-sectional image. Hence, it becomes easy to evaluate the spinal canal stenosis based on a shape shown in the extracted vertebral region.

Hereinafter, the second embodiment of the present invention will be described.

In the second embodiment, another example related to the process to extract a vertebral region in Step S102 will be described from among procedures for the spinal canal stenosis evaluation process (see FIG. 2) particularly in the first embodiment.

The respective processes other than extracting a vertebral region such as obtaining a spinal tomographic image group to be processed, calculating a length in the anteroposterior direction of an object in an extracted vertebral region, identifying a cross section including a spinous process, evaluating a stenosis, and displaying evaluation results are similar to the first embodiment. In the following description, the same descriptions as the first embodiment are omitted, and the different part (extracting a vertebral region) will be described.

Figure 17:
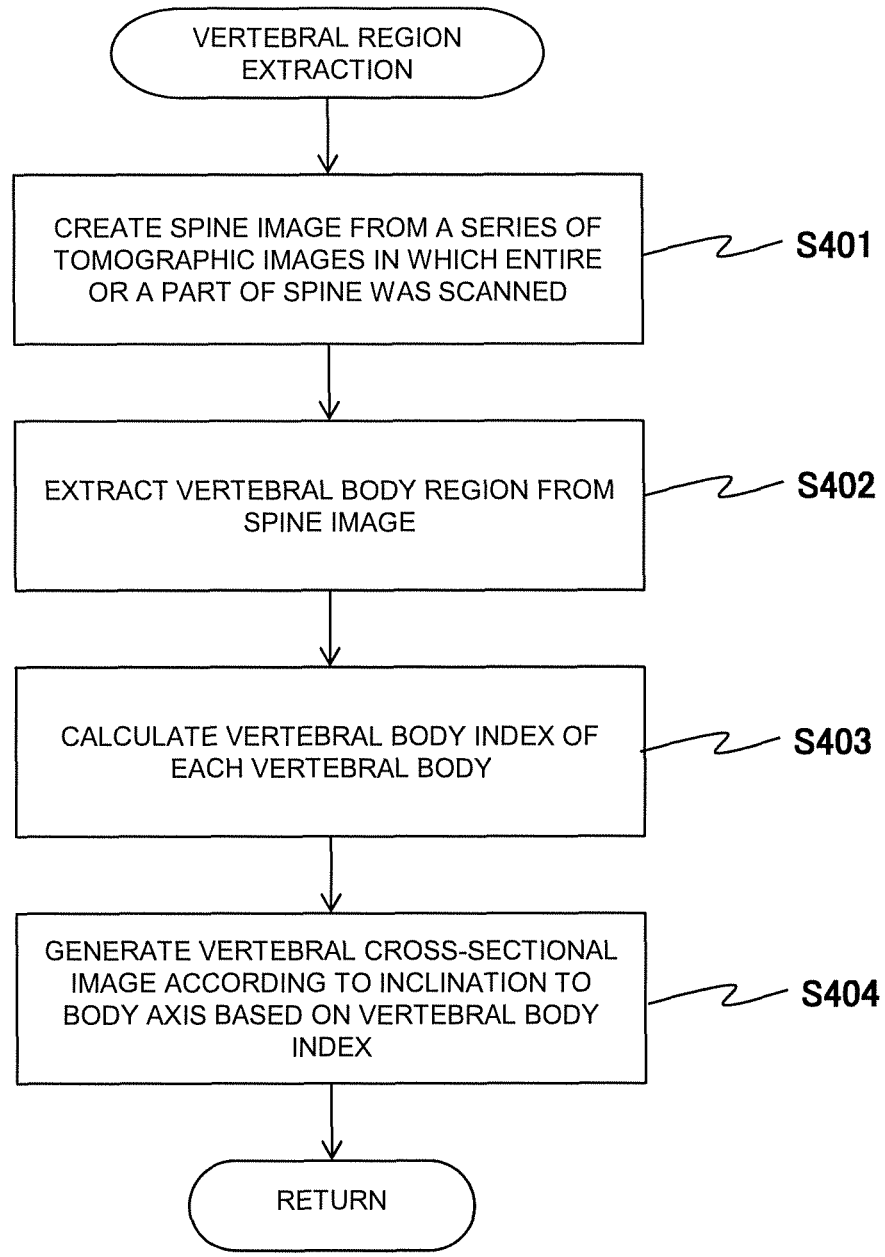
FIG. 17 is a flow chart explaining a flow of vertebral region extraction processing in case of extracting a vertebral region in a cross section according to a vertebral body inclination.

As shown in the flow chart of FIG. 17, the CPU 101 of the image processing device 100 of the second embodiment first generates the spine image 31 based on a series of tomographic images in which the spine of an object was scanned (Step S401). The spine image 31 is an image of a cross section along the spine. For example, the spine image 31 of the CPR image is generated as shown in FIG. 18(*a*). Alternatively, a sagittal image may be used for high-speed processing.

Figure 18:
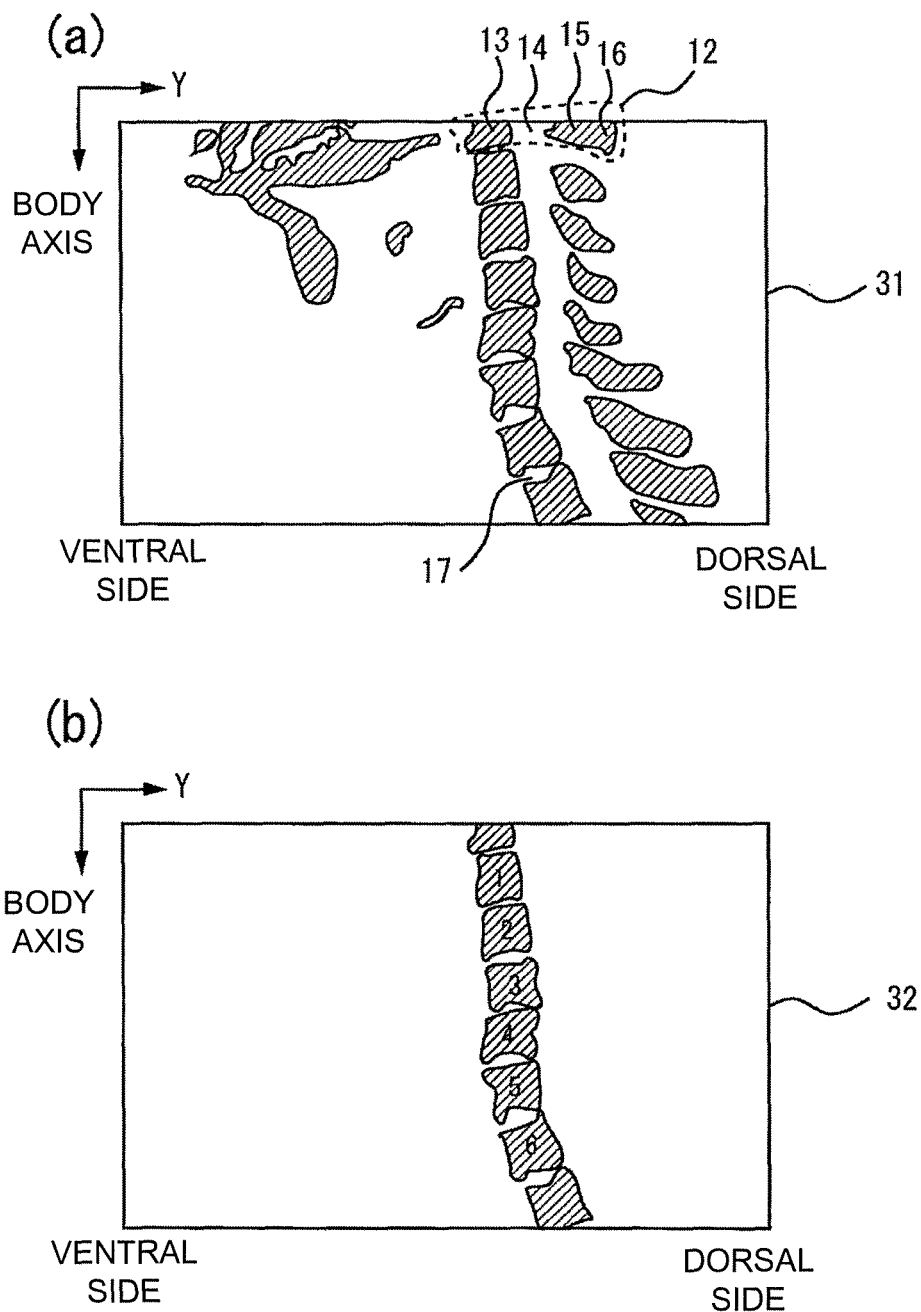
FIG. 18 is an explanatory diagram of Steps S401 and S402 in vertebral region extraction processing of FIG. 17.

FIG. 18(*a*) is a diagram showing an example of the spine image 31 generated in Step S401. The horizontal axis shows the Y direction (the anteroposterior direction of an object); the vertical axis shows the body-axis direction; the left side of the image shows the ventral side; and the right side shows the dorsal side. As shown in FIG. 18(*a*), a plurality of the vertebrae 12 are connected and displayed in the spine image 31. The vertebra 12 has the vertebral body 13 on the ventral side and the vertebral arch 15 as well as the spinous process 16 on the dorsal side, and there is the vertebral foramen 14 between the vertebral body 13 and the vertebral arch 15. Also, there is the intervertebral disc 17 between the vertebrae. The vertebral foramen 14 and the intervertebral disc 17 are regions other than bones.

The CPU 101 extracts a vertebral body region from the spine image 31 created in Step S401 (Step S402). That is, the CPU 101 binarizes the spine image 31 created in Step S401 by threshold processing. A threshold used for the binarization is set to a CT value separating bone regions from parts other than bones. In a binarized image to be generated, bone regions are set to "1", and the other regions are set to "0", for example. Then, the CPU 101 extracts a bone region on the ventral side from among bone regions in the created binarized image.

In order to extract only the bone region on the ventral side, the CPU 101 first scans bone regions in the body-axis direction.

If the scanned pixel is the pixel value "0" other than bone regions, the scanned pixel is converted into a bone region (the pixel value "1"). Hence, discontinuous bone regions are connected. Then, two bone regions with a predetermined length or more are generated in the image. The CPU 101 collectively extracts regions on the ventral side all together as vertebral body regions from among the connected regions.

Next, the CPU 101 restores the extracted vertebral body regions to the state before they were connected and recognizes the respective vertebral bodies individually by a labeling process. The labeling process results are shown in FIG. 18(*b*). The labeling numbers such as "1", "2", "3", "4", "5", and "6" are provided for the respective vertebrae.

The CPU 101 calculates the following vertebral body indexes for the labeled vertebral bodies respectively (Step S403). The vertebral body indexes to be calculated are a height, width, area, center of gravity, inclination, etc. of a vertebral body.

FIG. 19(*a*) is a diagram explaining the vertebral body indexes.

FIG. 19(*a*) is a diagram where the one vertebral body 13 of multiple vertebral bodies shown in FIG. 18(*b*) is enlarged. The horizontal axis shows the Y direction; the vertical axis shows the body-axis direction; and the direction perpendicular to the diagram shows the X direction. The straight line Yp shown in a broken line in the diagram is parallel to the Y axis.

A height and width of the vertebral body 13 can be calculated by searching around the vertebral body.

An area of the vertebral body 13 can be calculated by multiplying the calculated height and width together.

The center of gravity Q of the vertebral body 13 can be calculated from the calculated area.

The inclination θ of the vertebral body 13, for example, is an angle between the lower side (the straight line R-R') of the vertebral body 13 and the parallel line Yp.

After calculating the vertebral body indexes, the CPU 101 next generates vertebral cross-sectional images according to the vertebral body inclination based on the vertebral body indexes (Step S404). As an example of the method for creating the vertebral cross-sectional images, for example, the cross section D1 in which it passes through the center of gravity Q of the vertebral body 13 and an inclination from the Y axis becomes the inclination θ calculated by the above vertebral body indexes is determined, and then a cross-sectional image is created by obtaining pixel value data about the cross section D1 from the original tomographic image group. Although at least one of the vertebral cross-sectional images should be created for each vertebral body, a plurality of vertebral cross-sectional images may be created.

In case of creating a plurality of vertebral cross-sectional images, the second cross section D2 and the third cross section D3 parallel to the above cross section D1 are set. The distance d between the cross section D1 and the second cross sections D2 and D3 is set smaller than the half value of the height of the vertebral body 13. Also, a difference between an average height of all the vertebral bodies and a height of the targeted vertebral body 13 may be used as a coefficient in order to determine the distance d. Alternatively, a difference between an average area of all the vertebral bodies and an area of the targeted vertebral body 13 may be used as a coefficient in order to determine the distance d.

Thus, by determining a cross-sectional position of a vertebral cross-sectional image in light of vertebral body indexes of the other vertebral bodies, similar vertebral cross-sectional images for each vertebral body can be generated. Hence, even in a case where an appropriate evaluation image (an image to evaluate the spinal canal stenosis) for a targeted vertebral body cannot be obtained, it becomes easy to assume and interpolate the spinal canal shape by referring to information about the other vertebral cross-sectional images.

The CPU 101 generates a binarized image showing a vertebral region from the created vertebral cross-sectional images. A threshold used for binarization is set to a CT value separating a bone region and a part other than bones similarly to Step S302. Also, the binarized image to be generated sets a bone region to "1" and the other region to "0", for example.

As examples, the vertebral image 51 of FIG. 5(*a*) is created from the cross section D1 of FIG. 19(*b*); the vertebral image 52 of FIG. 5(*b*) is created from the cross section D2 of FIG. 19; and the vertebral image 53 of FIG. 5(*c*) is created from the cross section D3 of FIG. 19(*b*).

After vertebral cross-sectional images are created according to the inclination of vertebral bodies in the above processes, the CPU 101 executes processes Steps S103 to S107 of FIG. 2 based on the created vertebral cross-sectional images. That is, the CPU 101 calculates a length in the anteroposterior direction of an object in a vertebral image based on vertebral cross-sectional images created by vertebral region extraction processing of FIG. 17, identifies vertebral cross-sectional images including a spinous process based on the calculated length, calculates and evaluates various indexes for the spinal canal stenosis based on the identified vertebral cross-sectional images, and then displays the evaluation results.

Hence, because an image that is easy to evaluate the spinal canal stenosis can be created in light of the inclination of each vertebral body, highly accurate evaluation results can be obtained. Also, if a vertebral cross-sectional image is created using an appropriate cross section by referring to the other vertebral body information (vertebral body indexes), similar vertebral cross-sectional images for the respective vertebrae can be generated. This makes evaluation processing for the spinal canal simpler in the following steps. Also, this makes it easy to interpolate and assume the spinal canal shape in an image to be processed by referring to information about vertebral cross-sectional images of the other vertebral bodies.

[Third Embodiment]

In the third embodiment, another evaluation example in the spinal canal evaluation step (Step S106 of FIG. 2) will be described.

In the first and second embodiments, an image including a spinous process is identified, and the spinal canal that is to be a closed space is mainly set as an evaluation target. However, even if a closed space showing the spinal canal does not appear clearly on an image, the assumed spinal canal can be included as an evaluation target when the spinal canal position can be assumed from the other vertebral body images etc.

In the third embodiment, a closed space showing the spinal canal is drawn by interpolation in the vertebral images 52 and 53 where a closed space is not included as shown in FIGS. 5(*b*) and 5(*c*) for example, and an inequality between the left and right thicknesses of the spinal canal, a degree of the stenosis, etc. are analyzed based on the interpolated image.

Additionally, the closed space interpolation process can be applied to either of a tomographic image orthogonal to the body axis used in the first embodiment and a vertebral cross-sectional image used in the second embodiment.

The CPU 101 of the image processing device 100 calculates shape characteristics of a vertebral region after obtaining the vertebral images 51, 52, and 53 as shown in FIG. 5. The characteristics such as whether there is a closed space or not, whether there is a horizontal closing or not, and whether there is a vertical closing or not are calculated.

The CPU 101 assumes that there is a closed space if there is a region other than bones inside a bone region after scanning the vertebral images 51, 52, and 53 in the vertical and horizontal directions. Specifically, as a result of scanning in the horizontal direction, it is counted that there is a horizontal opening if there is a pixel array in the order of the pixel values "1 (bone)", "0 (the other)", and "1 (bone)". Similarly, as a result of scanning in the vertical direction, it is counted that there is a vertical opening if there is a pixel array in the order of the pixel values "1 (bone)", "0 (the other)", and "1 (bone)".

It is determined that there is a closed space in the vertebral image 51 of FIG. 5(*a*), a vertical opening in the vertebral image 52 of FIG. 5(*b*), and a horizontal opening in the vertebral image 53 of FIG. 5(*c*).

Next, the CPU 101 executes interpolation processing to create closed spaces in the vertebral images 52 and 53 where there are vertical and horizontal openings. As an example of the interpolation processing method, there is a method such as connecting two bone regions within a certain distance value.

FIG. 20(*a*) shows the interpolated image 52*a* for the vertebral image 52 having a vertical opening as shown in FIG. 5(*b*). As shown in FIG. 20(*a*), the CPU 101 draws the additional lines 68*a* and 68*b* between the vertebral body in the upper portion of the image and the spinous process in the lower portion of the image.

FIG. 20(*b*) shows the interpolated image 53*a* for the vertebral image 53 having a horizontal opening as shown in FIG. 5(*c*). As shown in FIG. 20(*b*), the CPU 101 draws the additional line 68*c* in a portion close to the lower portion in the bone region.

Thus, the closed spaces are created by interpolation in the vertebral images 52 and 53 having no closed spaces, which can perform evaluation for the spinal canal also in images that are excluded from the evaluation targets in the first embodiment and that does not include spinous processes as shown in FIGS. 5(*b*) and 5(*c*).

Also, by generating a closed space, in case of evaluating the spinal canal stenosis, a stenosis evaluation method for tubular organs such as blood vessels can be applied. A publicly-known example of the stenosis evaluation method for tubular organs, for example, is Patent Literature 1 etc. In Patent Literature 1, it is described that information about blood vessel shapes such as a blood vessel core line and a blood vessel contour point on a blood vessel orthogonal cross section is collected to calculate a local stenosis rate by correcting blood vessel torsion based on the collected information.

Additionally, the creation method of a closed space (spinal canal region) is not limited to the interpolation with additional lines described above. For example, an ellipse inscribed in the surrounding bone region (inscribed ellipse) is created from shapes of the vertebral images 52 and 53 having no closed spaces. Then, presuming that the inscribed ellipse shows the spinal canal in each vertebral image, a position, range, and degree of a stenosis are calculated.

The inscribed ellipse will be described by referring to FIG. 21. FIG. 21(*a*) shows an example for calculating the inscribed ellipse 71 corresponding to the vertebral image 52 of FIG. 5(*b*), and FIG. 21(*b*) shows an example for calculating the inscribed ellipse 72 corresponding to the vertebral image 53 of FIG. 5(*c*).

The CPU 101 calculates the lowest point P1 of the vertebral body (the bone region on the upper side of the image) from the vertebral image 52 shown in FIG. 21(*a*), the curve L2 on the upper side of the vertebral arch (the bone region on the upper side of the image), and the straight lines L3 and L4 whose left and right distances between the vertebral arch and the vertebral body are the shortest. Then, the ellipse 71 contacting the points in the range between the straight lines L3 and L4, a part of the curve L2, and the point P1 is created. However, a portion overlapping with the bone region in the created ellipse 71 is recognized as a region excluded from the assumed spinal canal.

Also, in the vertebral image 53 shown in FIG. 21(*b*), the CPU 101 sets the straight line L5 passing through the lowest point of the vertebral body from the vertebral image 53, the straight line L6 in a position where the width is maximized in a region (an open space) that is surrounded by the bone region but does not have a closing partly, and the straight line L7 in a position linearly symmetrical to the straight line L5 by setting the straight line L6 as the symmetry axis. Also, in order to create a rectangle where the open space is maximized, the straight lines L8 and L9 perpendicular to the straight lines L5 and L7 are set. Then, the ellipse 72 inscribed in the straight lines L5, L7, L8, and L9 is created. However, a portion overlapping with the bone region in the created ellipse 72 is recognized as a region excluded from the assumed spinal canal.

The CPU 101 calculates a position, range, and degree of a stenosis using the above publicly known method in the spinal canal region (closed space) recognized by the inscribed ellipses 71 and 72.

As described above, in the third embodiment, a closed space showing the spinal canal in a vertebral image including no closed space is calculated by interpolation to create a closed space in the vertebral image. Hence, the publicly known evaluation method used for evaluating a stenosis in blood vessels etc. can be applied to the spinal canal stenosis.

Although the suitable embodiments of the image processing device related to the present invention were described by referring to the attached diagrams, the present invention is not limited to such examples. It is obvious that a person skilled in the art can conceive various change examples or modification examples within the scope of technical ideas disclosed in the present application, and it is understood that such changes or modifications naturally belong to the technical scope of the present invention.

DESCRIPTION OF REFERENCE NUMERALS

1: image processing system, 100: image processing device, 101: CPU, 102: main memory, 103: storage device, 104: communication I/F, 105: display memory, 106: I/F, 107: display device, 108: mouse, 109: input device, 110: network, 111: image database, 112: medical image scanning apparatus, 113: bus, 12: vertebra, 13: vertebral body, 14: vertebral foramen, 15: vertebral arch, 16: spinous process, 21 and 22: binarized images, 23: image showing a vertebral region, 31: spine image, 32: image of labeled vertebral bodies, 40: spinal canal region, 41: top point in the spinal canal region, 42: end point on the ventral side in the vertebral region, 51, 52, and 53: vertebral images, 52*a* and 53a: interpolated images, 61: center of gravity, 62: principal axis of inertia, 63a, 63b, and 63c: lengths in the anteroposterior direction of an object in the vertebral region, 65: region other than bones, 67: separation line, 68a, 68b, and 68c: additional lines, 71 and 72: inscribed ellipses, 80, 80a, and 80b: evaluation result display windows, 81: operation input area, 82: evaluation target image display area, 83: spine image display area, 83a and 83b: vertebrae in which abnormalities are detected, 84: evaluation result list display area, 85: unfolded image display area, 85a: site of abnormalities, 86: alert display, 87: entire image of an object, 88: range displayed in the spine image display area 83, 90: reference curve

The invention claimed is:

1. An image processing device comprising:
a processor configured by one or more programs of executable instructions stored in a non-transitory medium, to comprise
an extraction unit extracting a vertebral region from a series of tomographic images in which at least a part of a spine of a subject was scanned,
a calculation unit calculating a length in an anteroposterior direction of the subject, for each cross section in the vertebral region extracted by the extraction unit,
a cross-section identifying unit identifying a cross section including a spinous process if the length in the anteroposterior direction of the subject in the vertebral region calculated by the calculation unit is larger than a predetermined reference value, and
a spinal canal stenosis evaluation unit evaluating a spinal canal stenosis by specifying a cross-sectional position of the cross-section identified by the cross-section identifying unit as a site to be analyzed; and
a display unit displaying evaluation results by the spinal canal stenosis evaluation unit,
wherein the spinal canal stenosis evaluation unit evaluates an asymmetry of a spinal canal shape in the cross section to be analyzed, as an evaluation index of the stenosis.

2. The image processing device according to claim 1, wherein the extraction unit extracts the vertebral region, for each tomographic image, and
the calculation unit calculates a length in the anteroposterior direction of the subject, for each vertebral region extracted from the series of tomographic images.

3. The image processing device according to claim 1, wherein the extraction unit generates vertebral cross-sectional images in cross sections according to the vertebral body inclination from a horizontal axis based on the series of tomographic images and extracts the vertebral region from the generated vertebral cross-sectional images, and
the calculation unit calculates a length in the anteroposterior direction of the subject, for each vertebral region extracted from the vertebral cross-sectional images.

4. The image processing device according to claim 1, wherein, if there is a closed space shape showing the spinal canal inside the extracted vertebral region in a cross section to be analyzed, the spinal canal stenosis evaluation unit evaluates the spinal canal stenosis based on the closed space shape.

5. The image processing device according to claim 1, wherein the spinal canal stenosis evaluation unit calculates a closed space showing the spinal canal by interpolation according to a vertebral region shape if the closed space showing the spinal canal is not included in the vertebral region and evaluates the spinal canal stenosis based on the closed space shape calculated by interpolation in a cross section to be analyzed.

6. The image processing device according to claim 1, wherein the spinal canal stenosis evaluation unit evaluates an inequality between a left thickness and a right thickness of the spinal canal in the cross section to be analyzed, as the evaluation index of the stenosis.

7. The image processing device according to claim 1, wherein the display unit displays a spine image where vertebrae are connected in a body-axis direction and distinguishably displays a vertebra that was determined to have a stenosis by the spinal canal stenosis evaluation unit in the spine image.

8. The image processing device according to claim 1, wherein the display unit displays an unfolded image of in a spinal canal and distinguishably displays a site that was determined to have a stenosis by the spinal canal stenosis evaluation unit in the unfolded image.

9. The image processing device according to claim 1, wherein the display unit lists and displays the evaluation results.

10. The image processing device according to claim 1, wherein the display unit displays a tomographic image in a cross section identified by the cross-section identifying unit.

11. A spinal canal evaluation method performed by an image processing device to evaluate a spinal canal stenosis, the method including:
an extraction step of extracting a vertebral region from a series of tomographic images in which at least a part of the spine was scanned,
a calculation step of calculating a length in an anteroposterior direction of an object for each cross section in the extracted vertebral region,
an identification step of identifying a cross section including a spinous process if the calculated length in the anteroposterior direction of an object in the vertebral region is larger than a predetermined reference value,
an evaluation step of evaluating, by a spinal canal stenosis evaluation unit of the image processing device, the spinal canal stenosis, by specifying a cross-sectional position of the cross-section identified in the identification step, as a site to be analyzed, and
a display step of displaying evaluation results obtained in the evaluation step, and
wherein the spinal canal stenosis evaluation unit of the image processing device evaluates, in the evaluation step, an asymmetry of a spinal canal shape in the cross section to be analyzed, as an evaluation index of the stenosis.

* * * * *